(12) United States Patent
Johnston et al.

(10) Patent No.: US 7,462,187 B2
(45) Date of Patent: Dec. 9, 2008

(54) POWERED SURGICAL APPARATUS, METHOD OF MANUFACTURING POWERED SURGICAL APPARATUS, AND METHOD OF USING POWERED SURGICAL APPARATUS

(75) Inventors: Constance Elaine Johnston, Eads, TN (US); Phillip Andrew Ryan, Memphis, TN (US); Carrie Deanne Mills, Atoka, TN (US); Perry Robin Mykleby, Collierville, TN (US); Andrew Christopher Burroughs, Kenosha, WI (US); Benjamin Leo Rush, Evanston, IL (US); Tasos George Karahalios, Chicago, IL (US); Jacob Shieffelin Brauer, Chicago, IL (US); Rodney Hal Monson, Winthrop Harbor, IL (US); Eric Christopher Sugalski, Chicago, IL (US); Dickon Isaacs, Chicago, IL (US); James Gerard Tappel, Hickory Corners, MI (US); Thomas Franz Enders, Mountain View, CA (US); Benjamin Mark Chow, San Francisco, CA (US); Energy Cruse, II, Foster City, CA (US); Scott Andrew Brenneman, Menlo Park, CA (US)

(73) Assignee: Gyrus ENT L.L.C., Bartlett, TN (US)

( * ) Notice: Subject to any disclaimer, the term of this patent is extended or adjusted under 35 U.S.C. 154(b) by 432 days.

(21) Appl. No.: 10/933,381

(22) Filed: Sep. 3, 2004

(65) Prior Publication Data
US 2005/0107814 A1    May 19, 2005

Related U.S. Application Data

(62) Division of application No. 10/103,104, filed on Mar. 22, 2002.

(60) Provisional application No. 60/366,224, filed on Mar. 22, 2002.

(51) Int. Cl.
*A61B 17/32* (2006.01)
*A61B 17/20* (2006.01)

(52) U.S. Cl. ............................ 606/170; 604/22; 604/35; 604/533

(58) Field of Classification Search ............... 604/22, 604/181; 606/167
See application file for complete search history.

(56) References Cited

U.S. PATENT DOCUMENTS 3,618,611 A    11/1971    Urban (Continued)

FOREIGN PATENT DOCUMENTS

EP    0 578 376 A1    1/1994
WO    WO 91/07138    5/1991

OTHER PUBLICATIONS

Typhoon™ Irrigated Cutter Blades, TreBay™ Medical Corporation brochure.

(Continued)

*Primary Examiner*—Kevin C Sirmons
*Assistant Examiner*—Andrew M Gilbert
(74) *Attorney, Agent, or Firm*—Oliff & Berridge, PLC

(57) ABSTRACT

A powered surgical apparatus can be used with a source of irrigation fluid and a source of suction. The powered surgical apparatus can include a cutting blade assembly and a handle. The handle can include an upper portion defining a distal section connectable to the cutting blade assembly and a lower portion extending downwardly from the upper portion. The handle can be connectable to the source of irrigation fluid and the source of suction. The system can also include a manually actuable input device that provides at least one signal relevant to at least one operation of the system, and a controller that receives the at least one input signal and provides an output signal to perform the at least one operation of the system.

21 Claims, 19 Drawing Sheets

U.S. PATENT DOCUMENTS

| | | | |
|---|---|---|---|
| 3,732,858 A | | 5/1973 | Banko |
| 3,734,099 A | | 5/1973 | Bender et al. |
| 3,776,238 A | * | 12/1973 | Peyman et al. ............... 606/171 |
| 3,844,272 A | * | 10/1974 | Banko ......................... 600/566 |
| 3,882,872 A | * | 5/1975 | Douvas et al. ............... 606/107 |
| 3,906,954 A | * | 9/1975 | Baehr et al. .................. 606/107 |
| 4,316,465 A | | 2/1982 | Dotson, Jr. .................... 604/22 |
| 4,428,748 A | * | 1/1984 | Peyman et al. ................. 604/22 |
| 4,517,977 A | | 5/1985 | Frost |
| 4,601,290 A | | 7/1986 | Effron et al. |
| 4,630,847 A | * | 12/1986 | Blenkush ...................... 285/29 |
| 4,694,828 A | * | 9/1987 | Eichenbaum ................... 606/6 |
| 4,700,702 A | * | 10/1987 | Nilsson ....................... 606/171 |
| 4,844,088 A | | 7/1989 | Kambin |
| RE33,258 E | | 7/1990 | Onik et al. |
| 4,955,882 A | * | 9/1990 | Hakky ......................... 606/14 |
| 5,176,677 A | * | 1/1993 | Wuchinich ................... 606/46 |
| 5,186,714 A | * | 2/1993 | Boudreault et al. ........... 604/21 |
| 5,286,253 A | | 2/1994 | Fucci |
| 5,395,312 A | | 3/1995 | Desai |
| 5,405,348 A | | 4/1995 | Anspach, Jr. et al. |
| 5,413,556 A | | 5/1995 | Whittingham |
| 5,490,860 A | | 2/1996 | Middle et al. |
| 5,492,527 A | | 2/1996 | Glowa et al. |
| 5,505,210 A | | 4/1996 | Clement |
| 5,520,634 A | | 5/1996 | Fox et al. |
| 5,569,254 A | | 10/1996 | Carlson et al. |
| 5,591,184 A | | 1/1997 | McDonnell et al. |
| 5,609,573 A | | 3/1997 | Sandock |
| 5,611,798 A | * | 3/1997 | Eggers ......................... 606/31 |
| 5,620,415 A | | 4/1997 | Lucey et al. |
| 5,685,838 A | | 11/1997 | Peters et al. |
| 5,697,158 A | | 12/1997 | Klinzig et al. |
| 5,712,543 A | | 1/1998 | Sjostrom |
| 5,792,167 A | | 8/1998 | Kablik et al. |
| 5,814,044 A | | 9/1998 | Hooven |
| 5,873,886 A | | 2/1999 | Larsen et al. |
| 5,899,915 A | | 5/1999 | Saadat |
| 5,957,881 A | | 9/1999 | Peters et al. |
| 5,957,937 A | * | 9/1999 | Yoon ........................... 606/147 |
| 5,984,939 A | | 11/1999 | Yoon |
| 5,993,464 A | | 11/1999 | Knodel |
| 6,042,593 A | | 3/2000 | Storz et al. |
| 6,099,494 A | * | 8/2000 | Henniges et al. .............. 604/35 |
| 6,139,554 A | * | 10/2000 | Karkar et al. ................ 606/131 |
| 6,149,622 A | * | 11/2000 | Marie ........................... 604/43 |
| 6,221,088 B1 | | 4/2001 | Bays |
| 6,293,957 B1 | | 9/2001 | Peters et al. |
| 6,375,635 B1 | * | 4/2002 | Moutafis et al. ............... 604/43 |
| 6,451,017 B1 | * | 9/2002 | Moutafis et al. ............... 606/41 |
| 6,689,146 B1 | * | 2/2004 | Himes ......................... 606/167 |
| 6,752,816 B2 | | 6/2004 | Culp et al. |
| 6,979,328 B2 | * | 12/2005 | Baerveldt et al. ............. 606/41 |
| 7,018,391 B2 | * | 3/2006 | Spitz et al. ................... 606/190 |

OTHER PUBLICATIONS

Wizard™ Micro Debrider, XOMED® Endoscopy Products brochure.

XPS™ Straightshot™ Micro Resector, XOMED® brochure.

Frost et al., "The design and development of an irrigating sucking cutter for neurosurgical use", *Engineering in Medicine*, vol. 15, No. 1, Jan. 1986, pp. 9-12.

Bleasel et al., "A new neurosurgical irrigating sucking cutter", *Journal of Neurosurgery*, vol. 65, No. 1, Jul. 1986, pp. 120-121.

Setliff et al., "The 'Hummer': New Instrumentation for Functional Endoscopic Sinus Surgery", *Am J Rinology*, vol. 8, Nov.-Dec. 1994, pp. 275-278.

* cited by examiner

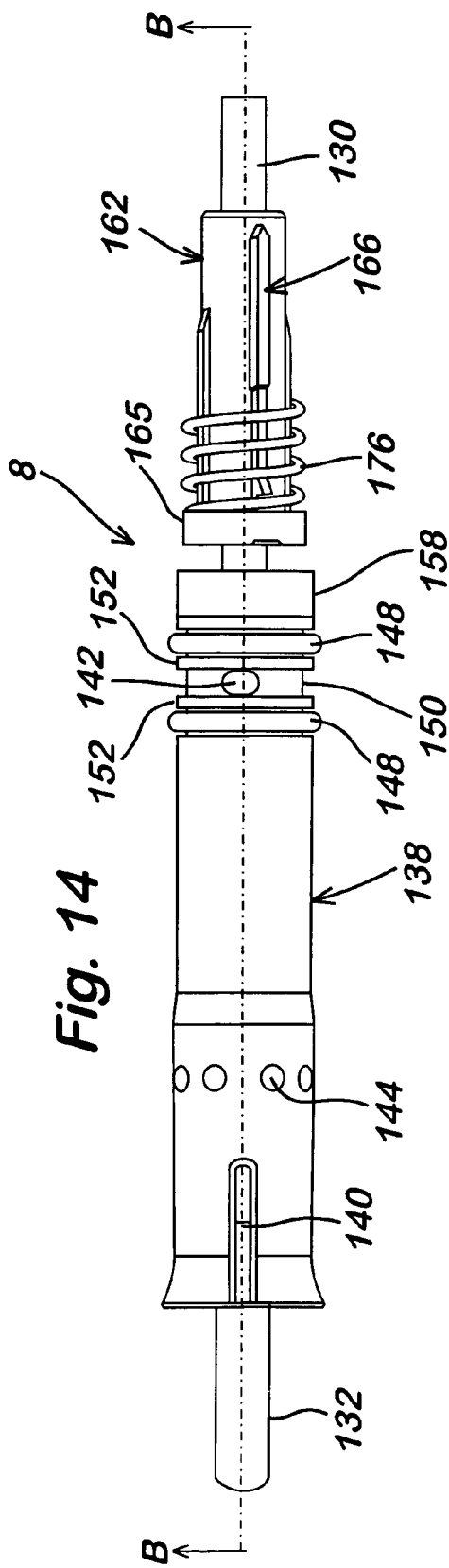
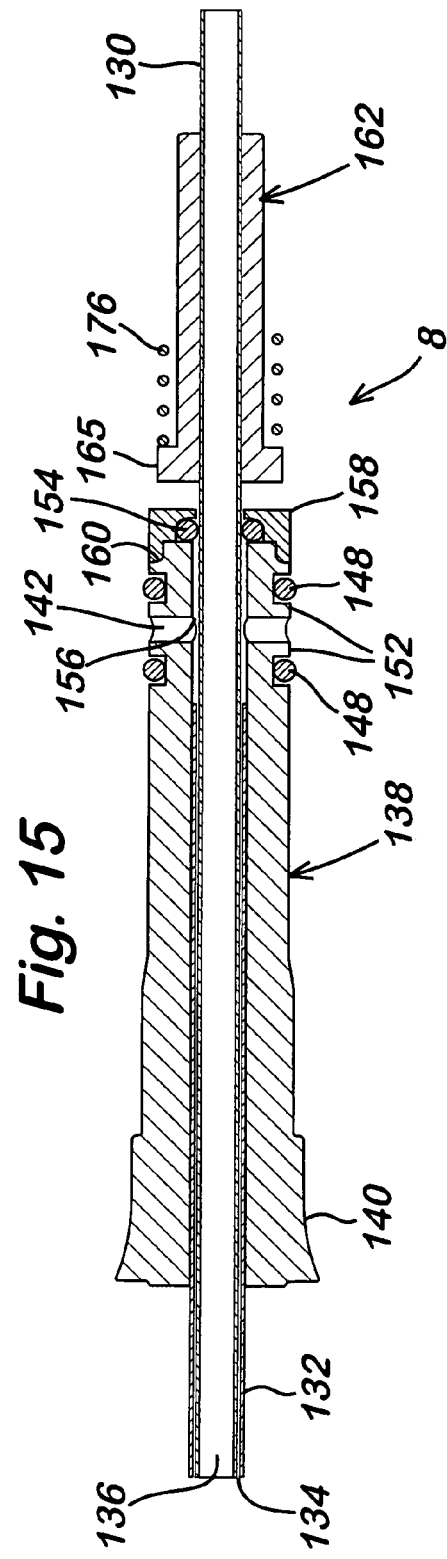

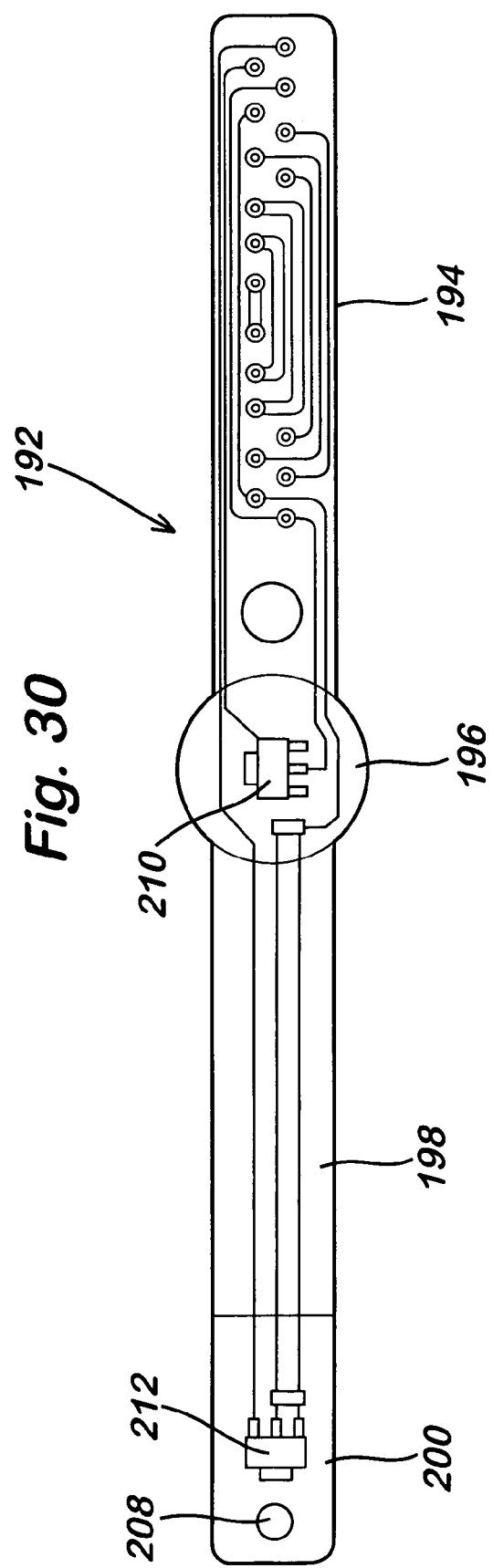

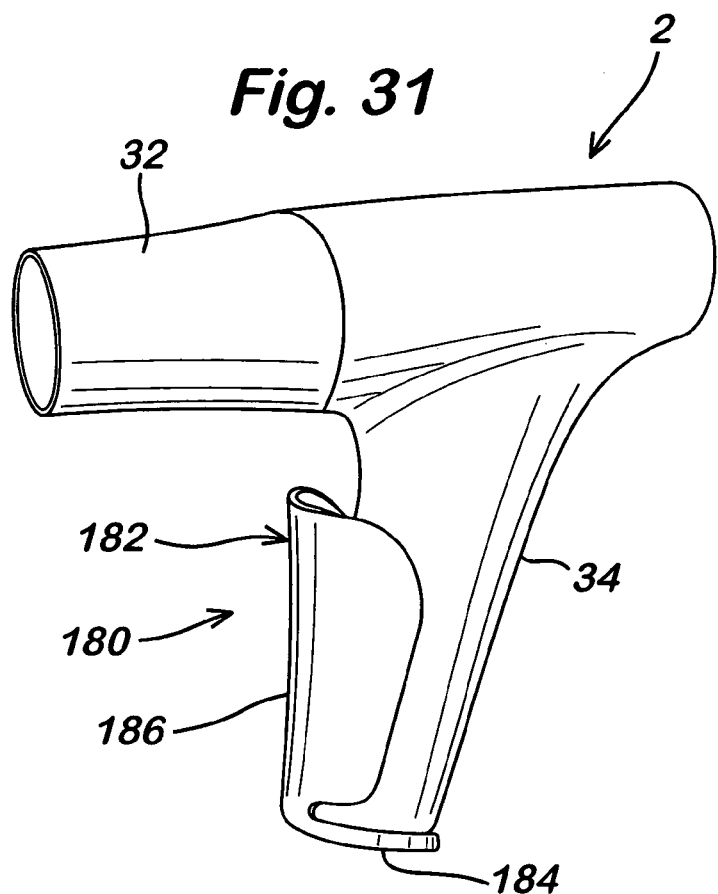
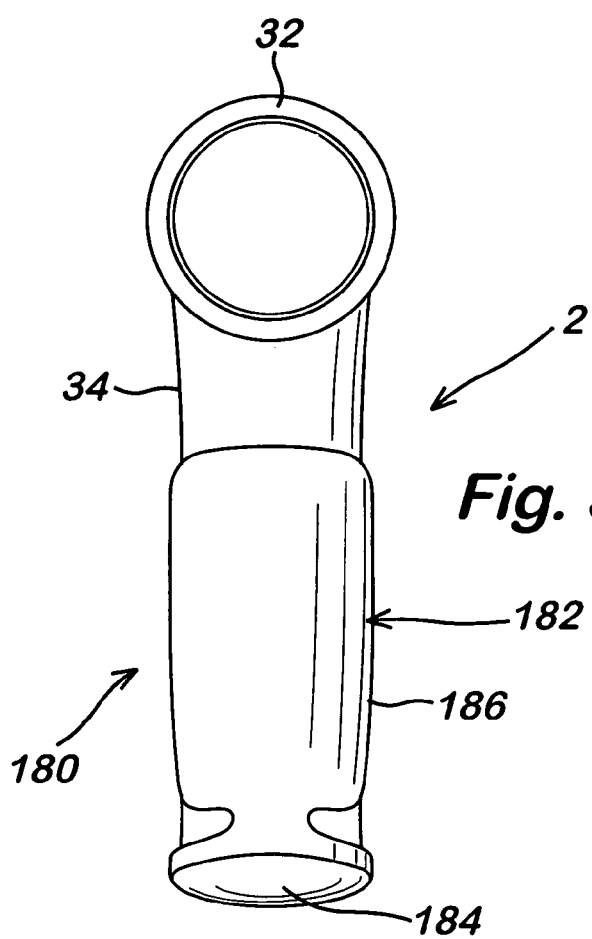

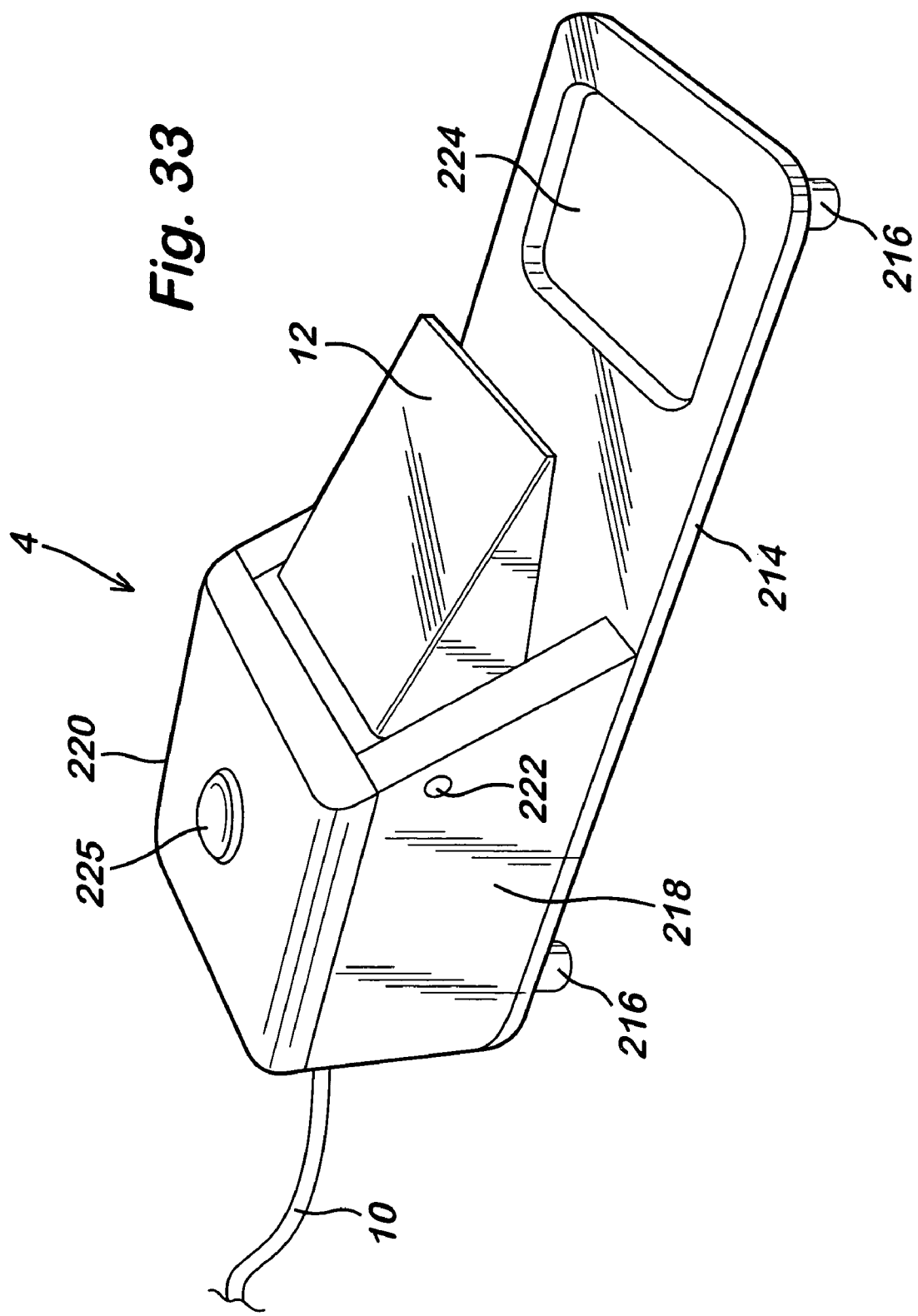

POWERED SURGICAL APPARATUS, METHOD OF MANUFACTURING POWERED SURGICAL APPARATUS, AND METHOD OF USING POWERED SURGICAL APPARATUS

This is a Division of application Ser. No. 10/103,104 filed Mar. 22, 2002, now U.S. Pat. No. 7,247,161 issued Jul. 24, 2007, which claims the benefit of U.S. Provisional Application No. 60/366,224 filed Mar. 22, 2002. The entire disclosure of the prior applications is hereby incorporated by reference herein in its entirety.

BACKGROUND OF THE INVENTION

1. Field of Invention

The invention relates to a powered surgical apparatus, a method of manufacturing the powered surgical apparatus, and a method of using the powered surgical apparatus. In particular, the invention relates to such a powered surgical apparatus usable to shave, cut and/or remove tissue, bone and/or any other bodily material.

2. Description of Related Art

Surgical apparatus are powered to enhance shaving, cutting and/or removal of tissue, bone and/or other bodily material. Such powered surgical apparatus can include a shaving or cutting instrument, such as a rotating blade, for example. The rotating blade can be connected to a handpiece which is held by an operator of the apparatus, such as a surgeon, for example. The surgeon, by holding the handpiece in the surgeon's hand, can thereby manipulate the rotating blade to shave or cut desired tissue, bone and/or other bodily material.

One example of such a surgical apparatus is disclosed in U.S. Pat. No. 5,492,527 (hereinafter "the 527 patent"), the entire disclosure of which is incorporated herein by reference. The 527 patent is specifically directed to a surgical shaver, for use in endoscopic surgical procedures, that drives an elongated rotatable surgical instrument and aspirates material from a surgical work site. As shown in FIGS. 1-5 and 14 of the 527 patent, the surgical shaver includes a handpiece 10 with a body 12 having a distal end 14, a proximal end 16, a collet assembly 18, a motor seal assembly 20 and a cable assembly 22. A shaver blade assembly 172, which is attached to the body 12 of the handpiece 10 by the collet assembly 18, includes an elongated rotatable inner blade 174 and an elongated outer blade 176. The elongated outer blade 176 defines a cutting window 188 facing a direction that is traverse to the axis of the shaver. The collet assembly 18 is manually rotatable to enable rotation of the cutting window 188.

In operation, a surgeon grasps the elongated body 12 of the handpiece 10 in a manner similar to gripping a writing apparatus, such as a pencil or pen. While gripping the body 12 of the handpiece 10 in this manner, the surgeon is able to direct the distal end of the shaver blade assembly to the bodily material to be cut. With the tips of the surgeon's fingers, the surgeon can also rotate the collet assembly 18 to rotate the cutting window 188 to an appropriate position to cut the bodily material.

SUMMARY OF THE INVENTION

However, the body of the handpiece of a surgical apparatus, such as the surgical shaver of the 527 patent, is typically more heavy than a common writing apparatus, such as a pencil or a pen. Thus, the hand muscles of an operator, such as a surgeon, used to grasp the body of the handpiece of the surgical apparatus in this manner may tire during a surgical operation, which can take a considerable amount of time. Also, the surgeon may find it difficult to rotate the collet assembly to move the cutting window of the outer blade while supporting the weight of the surgical apparatus by grasping the body of the handpiece as if it was a writing instrument. Further, the surgeon may find the operation of gripping the body of the handpiece of the surgical apparatus as if it was a writing apparatus to be otherwise cumbersome, unnatural or troublesome.

The invention addresses the above and/or other concerns and can provide a powered surgical apparatus, method of manufacturing the powered surgical apparatus, and method of using the powered surgical apparatus that facilitates ease of operation and/or promotes utility of operation. The invention can also provide apparatus and methods that facilitate and promote ease and effectiveness of cleaning and/or sterilization of at least a portion of the apparatus.

The invention can be used to cut, shave and/or remove tissue, bone and/or any other bodily material in a variety of surgical procedures, such as general ear, nose and throat (hereinafter "ENT"), head and neck, and oteneurologic procedures, for example. In accordance with one embodiment of the invention, it is used as a sinus debrider. However, the invention can be used in other surgical procedures. More specifically, the invention can be used in sinus procedures, such as ethmoidectomy/sphenoethmoidectomy, polypectomy, septoplasty, antrostomy, endoscopic DCR, frontal sinus drill-out, frontal sinus trephination and irrigation, septal spurs removal, and trans-sphenoidal procedures, for example. The invention can be used in nasopharyngeal/laryngeal procedures, such as adenoidectomy, laryngeal lesion de-bulking, laryngeal polypectomy, tracheal procedures, and tonsillectomy, for example. The invention can be used in head & neck procedures, such as soft tissue shaving, rhinoplasty (narrowing the bony valut and revision of the bony pyramid), removal of fatty (adipose) tissue (lipodebridement) in the maxillary and mandibular regions of the face, and acoustic neuroma removal, for example. The invention can also be used in otology procedures, such as mastoidectomy, and mastoidotomy, for example.

The above list of surgical operations and procedures is not intended to be exhaustive, and the surgical apparatus in accordance with the invention is intended to be used in any other applicable currently known or later developed surgical operation and procedure. In fact, the apparatus in accordance with the invention is not only intended to be used in surgical operations and procedures for humans, but can also be used in applicable surgical operations and procedures for animals and other organic matter.

However, even though the apparatus is intended to be usable in a variety of other applications, for convenience of explanation it is described below in the context of human surgery, such as ear, nose and throat surgery, and in particular sinus surgery. In this context, the apparatus and methods in accordance with the invention can be provided to comply with, but do not necessarily need to be provided to comply with, standards for surgical instruments, such as the following current voluntary standards: UL 2601-1: Medical Electrical Equipment, Part 1: General Requirements for Safety Australian Deviations, CSA 22.2 No. 601: Canadian Standards, IEC 601-1-1 (EN 60601-1): Medical Electrical Equipment, Part 1: General Requirements for Safety, IEC 601-1-2 (EN 60601-1-2) Medical Safety Equipment, Part 2: Particular Requirements for Safety, IEC 601-1-4 (EN 60601-1-2) Medical Electrical Equipment, Part 1: General Requirements for Safety 4. Collateral Standard: Programmable Electrical Medical Systems, IEC 61000-4-2: Electromagnetic Compatibility (EMC)—Part 4: Testing and Measurement Techniques—

Section 2: Electrostatic Discharge Immunity Test, IEC 61000-4-3: Electromagnetic Compatibility (EMC)—Part 4: Testing and Measurement Techniques—Section 3: Radiated, Radio Frequency, Electromagnetic Field Immunity Test, IEC 61000-4-4: Electromagnetic Compatibility (EMC)—Part 4: Testing and Measurement Techniques—Section 4: Electrical Fast Transient/Burst Immunity, IEC 61000-4-5: Electromagnetic Compatibility (EMC)—Part 4: Testing and Measurement Techniques—Section 5: Surge, IEC 529: Installation Protective Equipment, ISO 10993-1: Biological Evaluation of Medical Devices, and EN 55011 Limits and Methods of Measurement of Electromagnetic Disturbance Characteristics of Industrial, Scientific, and Medical (ISM) Radio-Frequency Equipment, Class B, for example. The apparatus and methods in accordance with the invention can also be provided to comply with other current standards and/or any later developed standards.

Various aspects of the invention are described below. These aspects are provided for exemplary purposes only, and should not be construed as limiting the scope of the invention.

I. Handle

The invention includes a handle that is usable as a powered surgical apparatus with a movable cutting blade assembly. The handle includes an upper portion defining a distal section connectable to the cutting blade assembly. The handle also includes a lower portion that extends downwardly from the upper portion so as to define an angle of less than 90° with the distal section of the upper portion.

This structure provides ergonomic advantages over other handle structures. For example, the operator of the above handle may grasp the handle as if was a pistol, and find the pistol grip easier to hold for long periods of time, easier to operate with one hand or easier to precisely manipulate the cutting blade assembly to its desired area, for example. The orientation of the lower portion relative to the upper portion also reduces, minimizes or prevents interference between the lower portion and the patient's chin during certain surgical procedures, such as sinus surgery. This orientation also enables at least one of a surgeon's fingers to be disposed at a position to facilitate manipulation of a collet assembly, which can be provided to form a distal section of the upper portion and enables rotation of a cutting window of the cutting blade assembly.

The invention also provides a method of manufacturing the above handle. The method includes forming an upper portion having a distal section that is connectable to the movable cutting blade assembly, and connecting a lower portion to the upper portion such that the lower portion extends downwardly from the upper portion so as to define an angle of less than 90° with the distal section of the upper portion.

The invention also provides a handle that is usable as a powered surgical apparatus with a movable cutting blade assembly and a source of irrigation fluid. The handle includes an upper portion defining a distal section connectable to the cutting blade assembly. The upper portion includes a proximal end that defines an irrigation fluid coupling that is connectable to the source of irrigation fluid. The upper portion defines an irrigation fluid channel that extends from the irrigation fluid coupling to the cutting blade assembly. The handle also includes a lower portion that extends downwardly from the upper portion.

This handle provides various advantages. For example, this handle provides ergonomic advantages while also enabling the use of irrigation fluid.

The invention also provides a method of manufacturing this handle. The method includes forming an upper portion having a distal section that is connectable to the movable cutting blade assembly, forming an irrigation fluid coupling that is connectable to the source of irrigation fluid at a proximal end of the upper portion, forming an irrigation fluid channel from the irrigation fluid coupling to the cutting blade assembly, and connecting a lower portion to the upper portion so as to extend downwardly from the upper portion.

II. Handle Assembly

The invention also provides a handle assembly that is usable as a powered surgical apparatus with a movable cutting blade assembly and a source of irrigation fluid. The handle assembly includes a handle having a distal section that is connectable to the movable cutting blade assembly. The handle includes a proximal end that defines an irrigation fluid coupling. The handle defines an irrigation fluid channel that extends from the irrigation fluid coupling to the cutting blade assembly. The handle assembly also includes a connector that is connectable to the proximal end of the handle at the irrigation fluid coupling. The connector defines an irrigation fluid entry channel that is contiguous with the irrigation fluid channel of the handle.

This invention provides various advantages. For example, utilizing the connector obviates connecting the source of irrigation fluid directly to the cutting blade assembly. Thus, the source of irrigation fluid does not need to be detached from the handle assembly when the cutting blade assembly is changed.

The invention also provides a method of manufacturing this handle assembly. The method includes forming a handle having a distal section that is connectable to the movable cutting blade assembly, forming an irrigation fluid coupling at a proximal end of the handle, forming an irrigation fluid channel in the handle from the irrigation fluid coupling to the cutting blade assembly, connecting a connector to the proximal end of the handle at the irrigation fluid coupling, and forming an irrigation fluid entry channel in the connector that is contiguous with the irrigation fluid channel of the handle.

The invention also provides a handle assembly that is usable as a powered surgical apparatus with a movable cutting blade assembly. The handle assembly includes an upper portion defining a distal section that is connectable to the cutting blade assembly and a lower portion that extends downwardly from the upper portion. The handle assembly also includes a trigger switch assembly that is connected to the lower portion that provides at least one output signal relevant to operation of the powered surgical apparatus.

This handle assembly provides various advantages. For example, because of its disposition on the lower portion of the handle, the trigger switch assembly can be easier to operate than other types of actuating mechanisms, such as a footswitch, for example.

The invention also provides a method of manufacturing this handle assembly. The method includes forming an upper portion that has a distal section connectable to the cutting blade assembly, connecting a lower portion to the upper portion so as to extend downwardly from the upper portion, and connecting a trigger switch assembly to the lower portion that provides at least one output signal relevant to operation of the powered surgical apparatus.

III. Cutting Blade Assembly

The invention also provides a cutting blade assembly that is usable with a handle as a powered surgical apparatus. The handle can have an interior surface that defines at least one channel and a motor that rotates the interior surface. The cutting blade assembly includes an outer tube defining a cutting window and an outer hub secured to the outer tube.

The cutting blade assembly also includes an inner tube that extends within the outer tube and defines a cutting surface. The cutting blade assembly also includes an inner hub that is secured to the inner tube. The inner tube defines an exterior and at least one drive spline extending longitudinally along the exterior. The at least one drive spline communicates with the at least one channel of the handle to enable rotation of the inner hub and the inner tube.

This cutting blade assembly provides various advantages. For example, the communication between the at least one drive spline and the at least one channel provides sufficient surface area to effectively communicate the motor torque to the inner hub.

The invention also provides a method of manufacturing this cutting blade assembly. The method includes forming an outer tube that includes a cutting window, securing an outer hub to the outer tube, forming an inner tube that defines a cutting surface, extending the inner tube within the outer tube, securing the inner tube to an inner hub, and forming at least one drive spline that extends longitudinally on an exterior of the inner hub, wherein the at least one drive spline communicates with the at least one channel of the handle to enable rotation of the inner hub and the inner tube.

The invention also provides a cutting blade assembly that is usable with a handle as a powered surgical apparatus. The handle can include a manually rotatable collet assembly and at least one retention ball. The cutting blade assembly includes an inner tube defining a cutting surface, an inner hub secured to the inner tube, an outer tube defining a cutting window such that the inner tube extends within the outer tube, and an outer hub that is secured to the outer tube. The outer hub has an exterior that defines at least one dimple that is engageable with the at least one retention ball to secure the outer hub to the collet assembly.

This cutting blade assembly provides various advantages. For example, the communication between the at least one retention ball and the at least one dimple provides increased surface area to effectively secure the outer hub to the collet assembly.

The invention also provides a method of manufacturing this cutting blade assembly. The method includes forming an inner tube that defines a cutting surface, securing the inner tube to an inner hub, forming an outer tube that defines a cutting window, extending the inner tube within the outer tube, securing the outer tube to the outer hub, and forming at least one dimple in an exterior of the outer hub that is engageable with the at least one retention ball to secure the outer hub to the collet assembly.

The invention also provides a cutting blade assembly that is usable with a handle and a source of irrigation fluid as a powered surgical apparatus. The handle can include a barrel that defines an irrigation fluid channel that defines a longitudinal section and a transverse section. The cutting blade assembly includes an inner tube defining a cutting surface, an inner hub secured to the inner tube, an outer tube defining a cutting window such that the inner tube extends within the outer tube so as to define a tube gap therebetween, and an outer hub secured to the outer tube. The outer hub defines a transverse through hole that communicates with the transverse section of the irrigation fluid channel of the barrel and the tube gap, such that irrigation fluid can flow through the irrigation fluid channel of the barrel into the tube gap via the transverse through hole of the outer hub.

This cutting blade assembly provides various advantages. For example, the cutting blade assembly provides a structure that does not require the source of irrigation fluid to directly be connected to it, which enables the cutting blade assembly to be changed without requiring that the source of irrigation fluid be disconnected from the handle.

The invention also includes a method of manufacturing this cutting blade assembly. The method includes forming an inner tube that defines a cutting surface, securing an inner hub to the inner tube, forming an outer tube that defines a cutting window, extending the inner tube within the outer tube so as to define a gap therebetween, securing an outer hub to the outer tube, and forming a transverse through hole in the outer hub that communicates with the transverse section of the irrigation fluid channel of the barrel and the tube gap, such that irrigation fluid can flow through the irrigation fluid channel of the barrel into the tube gap via the transverse through hole of the outer hub.

IV. Powered Surgical Apparatus System

The invention also provides a powered surgical apparatus system for use with a source of irrigation fluid and a source of suction. The system includes a cutting blade assembly and a handle. The handle includes an upper portion defining a distal section connectable to the cutting blade assembly and a lower portion extending downwardly from the upper portion. The handle is connectable to the source of irrigation fluid and the source of suction. The system also includes a manually actuable input device that provides at least one signal relevant to at least one operation of the system, and a controller that receives the at least one signal and provides an output signal to perform the at least one operation of the system.

The powered surgical apparatus system provides various advantages, such as advantages discussed above, for example.

These and other features and advantages of this invention are described in, or are apparent from, the following detailed description of various exemplary embodiments of the systems and methods according to this invention.

BRIEF DESCRIPTION OF THE DRAWINGS

Various exemplary embodiments of this invention will be described in detail, with reference to the following figures, wherein:

FIG. 14 is a partial perspective view showing a portion of the exterior of the cutting blade assembly 8;

FIG. 15 is a sectional view of the cutting blade assembly 8 taken along plane B-B of FIG. 14;

FIG. 30 is a schematic of the sensor strip 192 of the trigger switch assembly 180;

FIG. 31 is a side perspective view of the trigger switch assembly mounted on the handle 2;

FIG. 32 is a front schematic view of the trigger switch assembly 180 mounted on the handle 2;

FIG. 33 is a perspective view showing the exterior of the footswitch 4;

DETAILED DESCRIPTION OF PREFERRED EMBODIMENTS

For convenience of explanation, exemplary embodiments of the invention are described below with reference to the figures in the context of human surgery, such as ear, nose and throat surgery, and in particular sinus surgery. However, as previously discussed, all exemplary embodiments of the invention are intended to be used in any applicable field of endeavor.

I. Overall System Description

Figure 1:
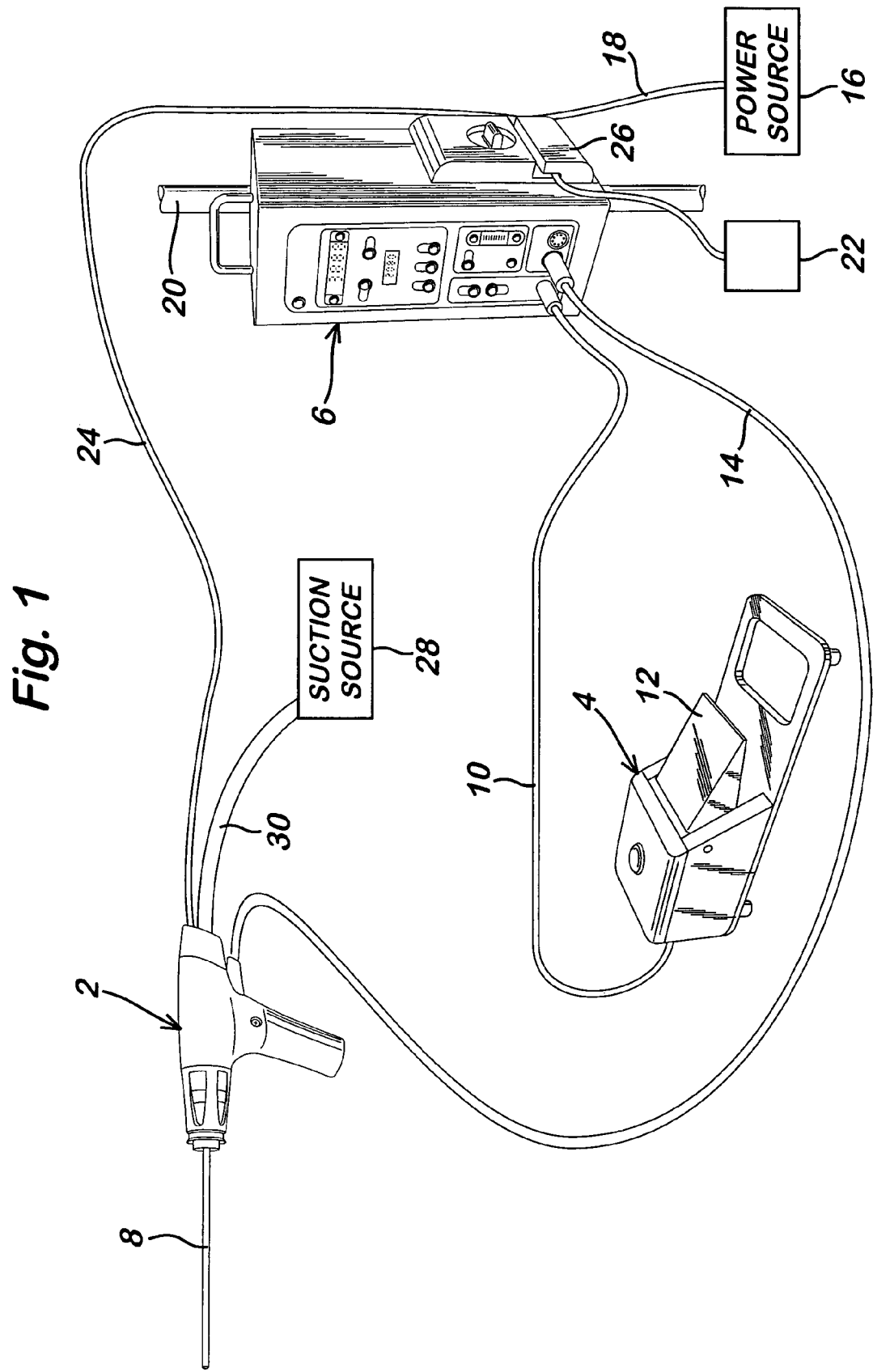
FIG. 1 is a schematic of a powered surgical apparatus in accordance with an exemplary embodiment of the invention.

FIG. 1 is a schematic of a powered surgical apparatus 1 in accordance with an exemplary embodiment of the invention. As shown in FIG. 1, the apparatus 1 includes a handle 2, a footswitch 4 and a controller 6. A general description of these elements as well as their interrelationship is provided below.

The handle 2 includes a cutting blade assembly 8 at its distal end. The distal end of the cutting blade assembly 8 is usable to cut, shave and/or remove bodily material during a surgical procedure or operation. The distal end of the cutting blade assembly 8 can perform the cutting, shaving and/or removal in any manner, such as by rotation, for example. In operation, a surgeon grasps the handle 2 as if grasping a pistol and brings the distal end of the cutting blade assembly 8 into contact with the bodily material to be shaved, cut and/or removed.

The footswitch 4 is connected to the controller 6 via a footswitch signal line 10, such as an electric cable, for example. The footswitch 4 is typically disposed on the floor of a surgical room within reach of the surgeon's foot. The footswitch 4 includes an actuator member, such as a foot pedal 12, the actuation of which results in an input signal being transmitted to the controller 6 via the footswitch signal line 10. In operation, the surgeon places his or her foot on the footswitch 4 and depresses the foot pedal 12 to provide an input signal to the controller for the purpose of controlling at least one operation of the apparatus, such as energizing/de-energizing rotation of the cutting blade assembly 8, or speed of rotation of the cutting blade assembly 8, for example. However, the footswitch signal line 10 can be used for any other purpose, such as to transmit other types of signals to the controller 6, to transmit signals from the controller 6 to the footswitch 4, or to supply power to the footswitch 4, for example.

A trigger switch assembly (not shown in FIG. 1) can be attached to the handle 2 and used in lieu of, or in addition to, the footswitch 4. The trigger switch assembly can be actuable such that, while the surgeon grasps the handle as if grasping a pistol, one or more of the surgeon's fingers can press a part of the trigger switch assembly toward the handle as if pulling the trigger of the pistol.

The controller 6 is also connected to the handle 2 via a handle signal line 14, such as an electric cable, for example. The controller 6 can output signals to the handle via the handle signal line 14, such as control signals controlling on/off status of the cutting blade assembly, and/or rotation speed of the cutting blade assembly 8 based upon input signals received by the controller 6 from the footswitch 4, for example.

However, the handle signal line 14 can be used for any other purpose, such as to transmit other types of signals to the handle 2, to transmit signals from the handle 2 to the controller 6, or to supply power to the handle 2, for example. For example, the handle supply line 14 can be used to transmit signals to the controller 6 indicating the type of handle 2 that is currently connected to the controller 6.

The controller 6 is also connected to a power source 16 via a power source supply line 18, such as a standard electric cable or hospital grade power cord, for example. The controller 6 receives and utilizes a source of AC electric voltage from the power source 16. However, the controller can also receive and utilize a source of DC electric voltage. Further, the AC or DC power source 16 does not have to be remote from the controller 6, and instead can be integral therewith.

As shown in FIG. 1, the controller 6 can be slidably disposed on a vertical rail 20. Slidably disposing the controller 6 on the vertical rail 20 enables the mounting height of the controller to adjusted to facilitate viewing data on the face of the controller, to take into account space constraints, or for any other purpose.

However, the controller 6 does not have to be mounted on the vertical rail 20. Instead, the controller can be mounted on a horizontal rail. In fact, the controller 6 can be disposed and/or mounted in any manner or location. The controller can even be mounted at a location remote from the surgical room or location of the other elements of the surgical apparatus.

The handpiece can be connected to a source of irrigation fluid 22 by an irrigation fluid supply tube 24. The irrigation fluid can be provided to travel through the handle 2 and to the cutting blade assembly 8 and/or the surgical site for the purpose of lubricating the blade or blades for enhanced cutting or shaving efficiency, for example. However, the irrigation fluid can be provided for any other purpose, such as flushing out the surgical site for enhanced removal of cut or shaven bodily material, for example.

The irrigation fluid can be supplied from the irrigation fluid source 22 to the handle 2 by any method. For example, the irrigation fluid may be supplied to the handle 2 by an irrigation fluid supply mechanism 26 disposed on a side of the controller 6.

The handle 2 can also be connected to a source of suction 28 by a suction supply tube 30. The suction can be provided so as to extend through the handle 2 and to the cutting blade assembly 8 and/or the surgical site for the purpose or removing cut or shaven bodily material and/or irrigation fluid, for example. However, the suction can be provided for any other purpose.

The above overall system description of the apparatus 1 is provided for exemplary purposes only. The invention is not only intended to cover the above described overall system, but also various other aspects of the individual elements or combinations of the individual elements of the overall system. Thus, any of the other aspects of the individual elements of the invention can be utilized individually, with combinations of the above individual elements or in conjunction with systems that are quite different than the overall system discussed above and still be within the spirit and scope of the invention.

II. Handle

Figure 2:
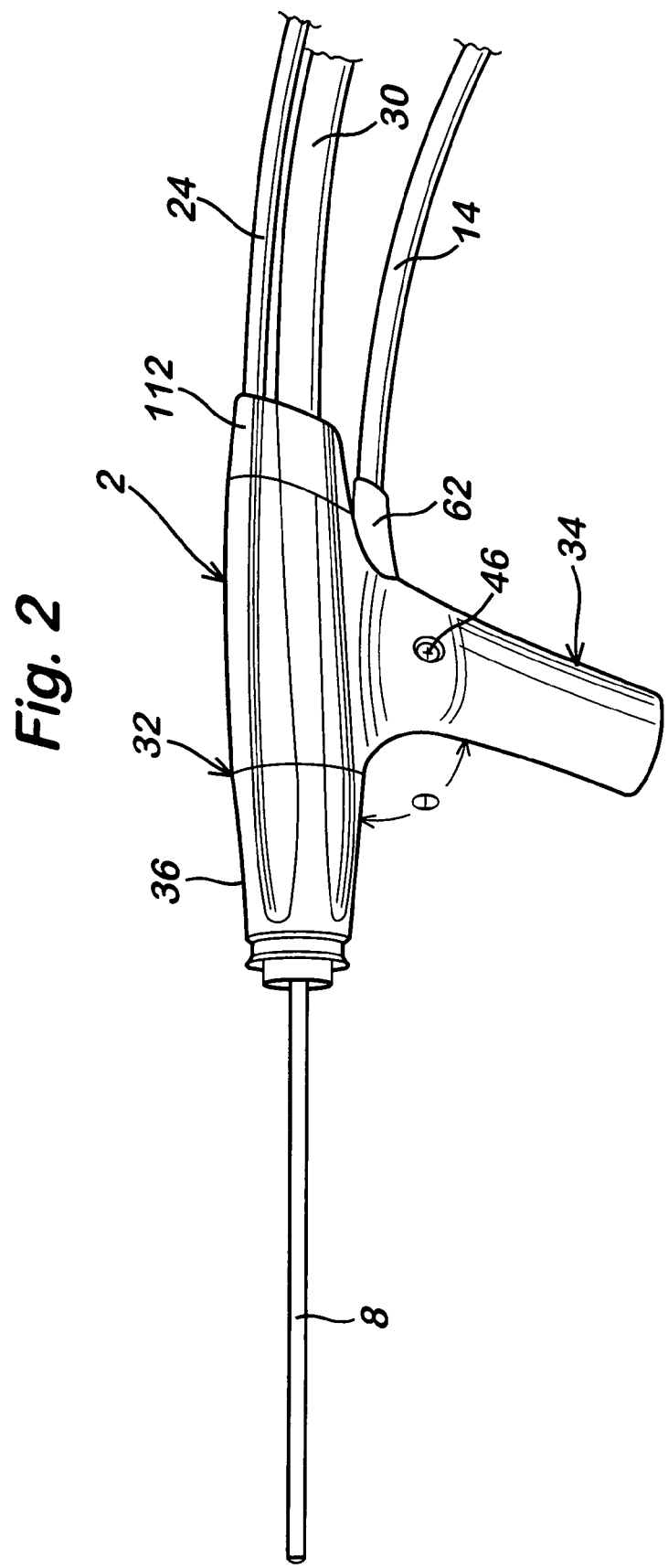
FIG. 2 is a schematic showing the exterior of the handle 2.
Figure 3:
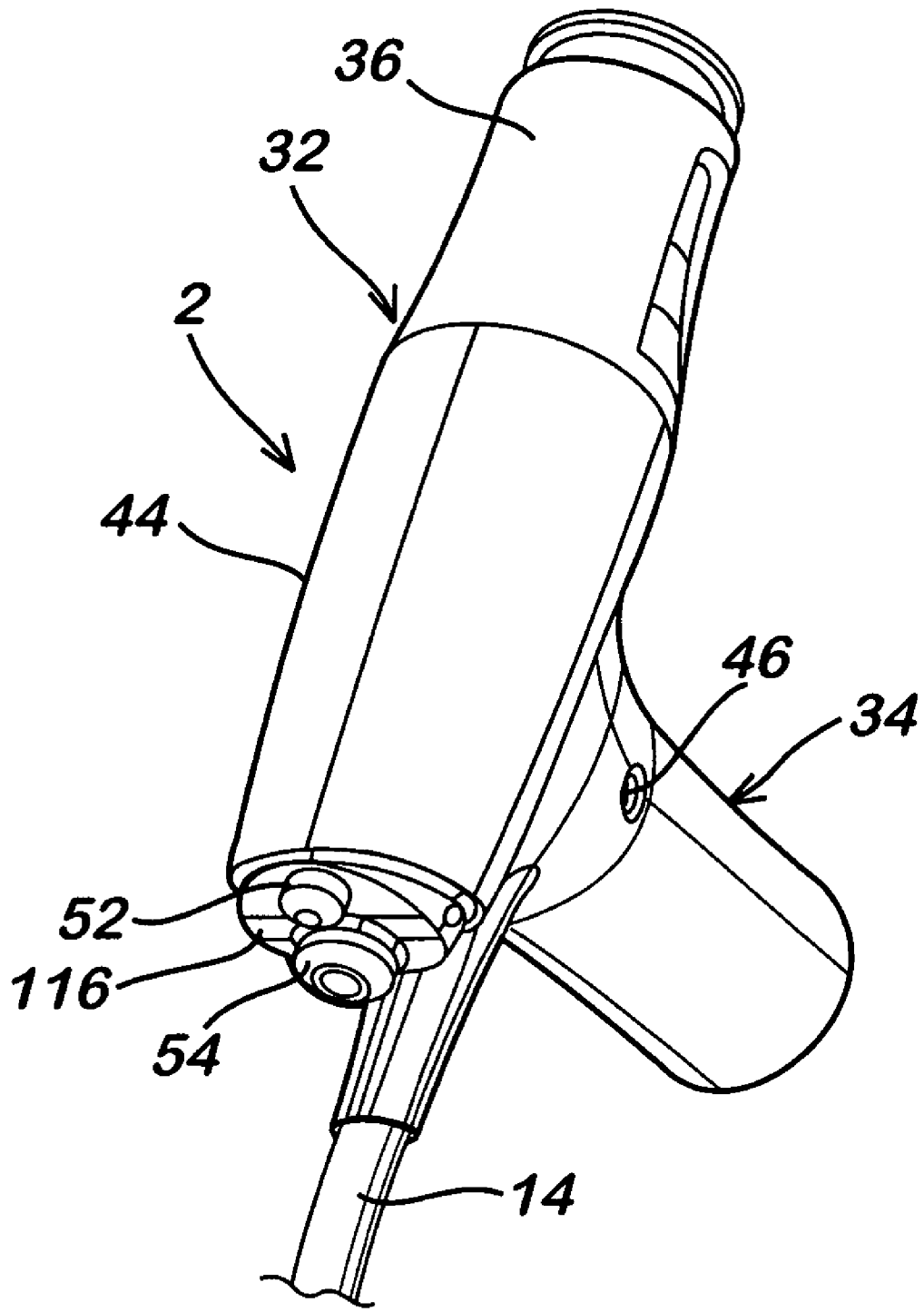
FIG. 3 is a perspective view of the exterior of the handle 2.
Figure 4:
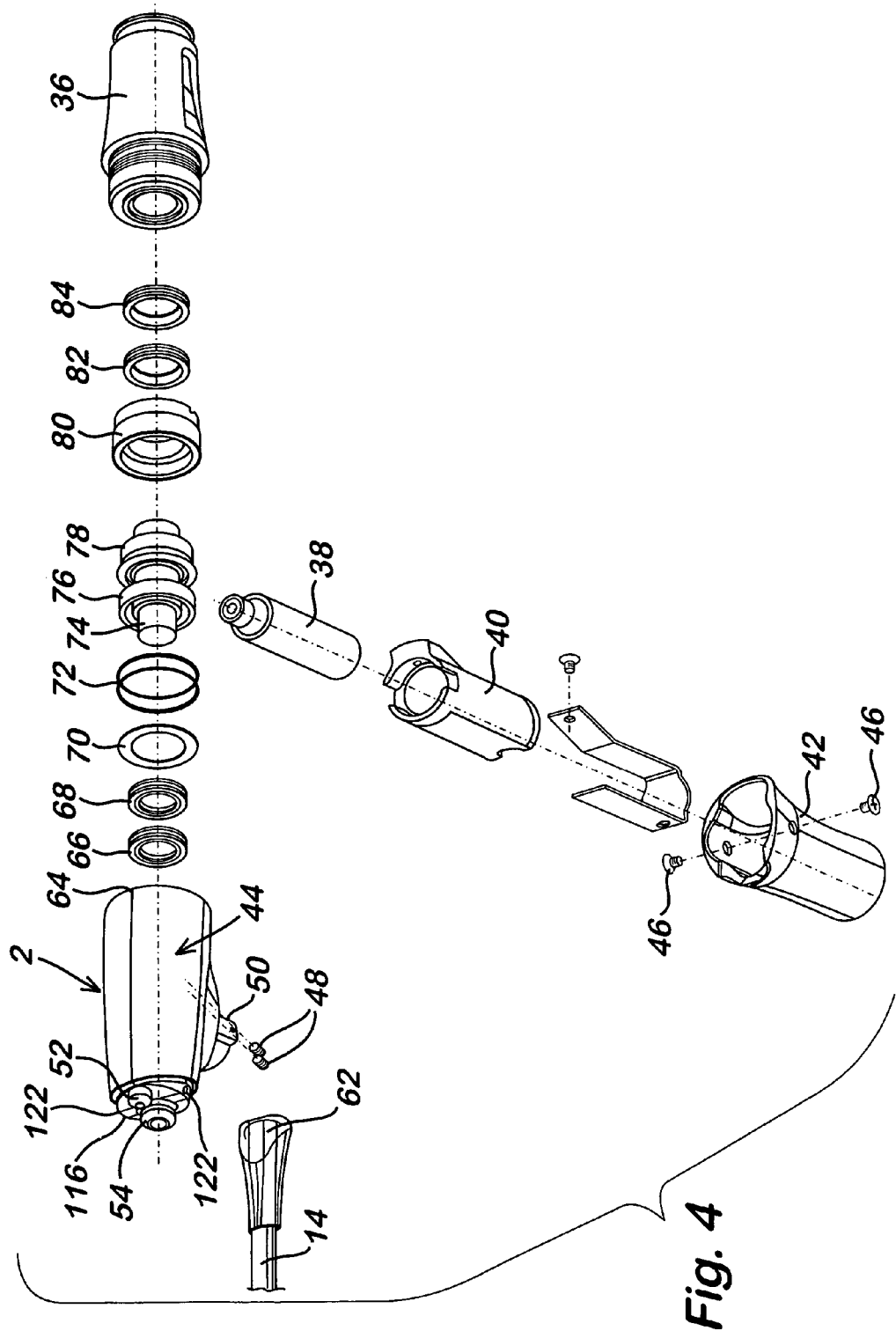
FIG. 4 is an exploded perspective view showing various sub-elements of the handle 2.
Figure 5:
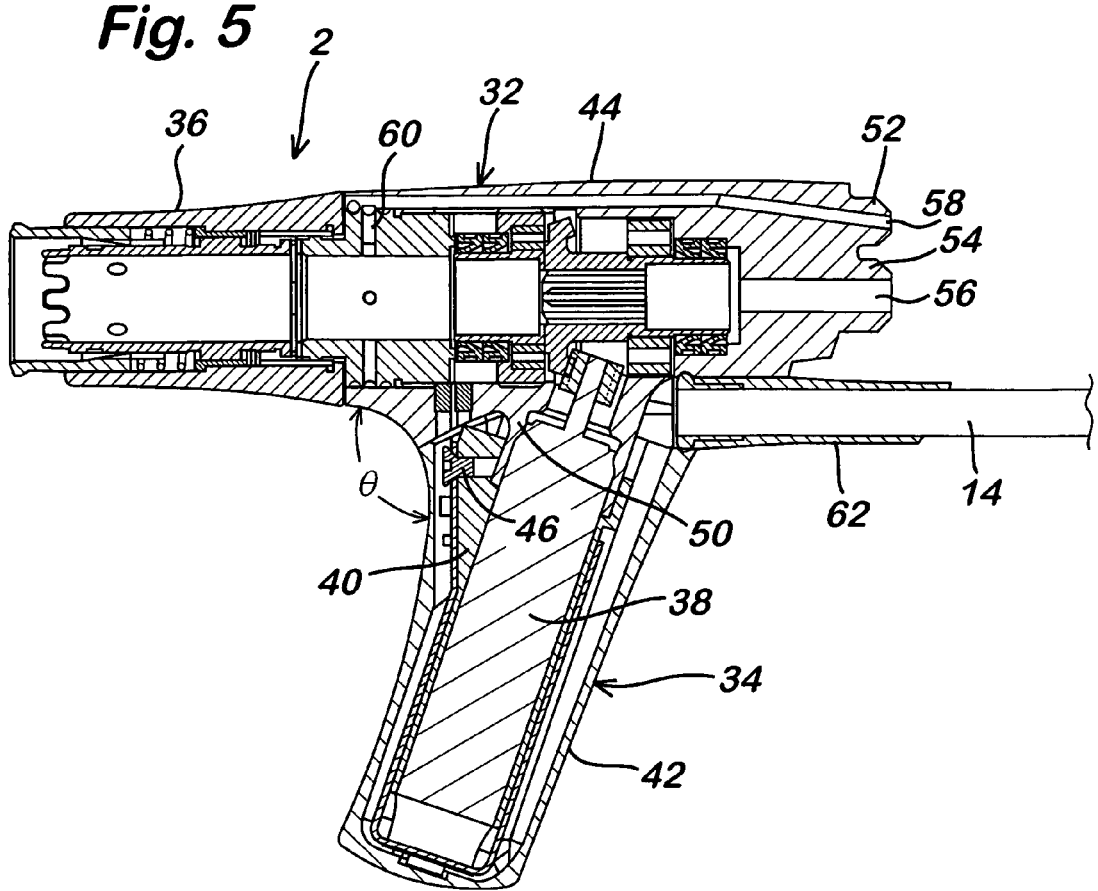
FIG. 5 is a sectional side view showing various sub-elements of the handle 2.
Figure 6:
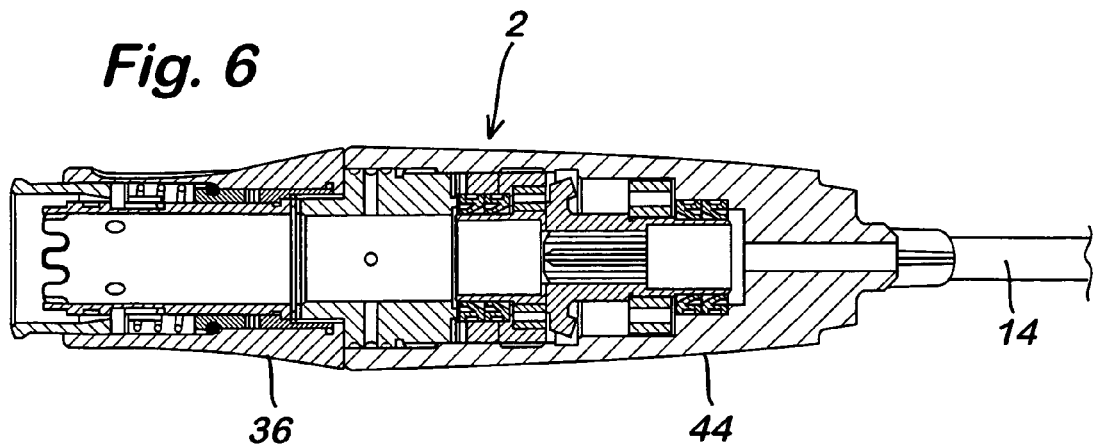
FIG. 6 is a sectional top view showing various sub-elements of the handle 2.

Various views of exemplary embodiment of the handle 2 are shown in FIGS. 2-6, wherein FIG. 2 is a schematic showing the exterior of the handle, FIG. 3 is a perspective view of the exterior of the handle, FIG. 4 is an exploded perspective view showing various sub-elements of the handle 2, FIG. 5 is a sectional side view showing various sub-elements of the handle 2, and FIG. 6 is a sectional top view showing various sub-elements of the handle 2. An exemplary embodiment of the handle 2 is described below in conjunction with FIGS. 2-6.

The handle 2 includes an upper portion 32 and a lower portion 34 that define a pistol grip. The operator, such as a surgeon, grasps the handle 2 as if gripping a pistol. The specific manner of grasping the handle 2 may be determined by the operator's preference. However, an exemplary method of grasping the handle 2 is described below. For example, when grasping the handle 2, the surgeon's palm can be pressed against a rear end of the lower portion 34, while one or more of the surgeon's fingers can wrap around a front end of the lower portion 34. One or more of the surgeon's fingers may also extend along the upper portion 32.

The pistol grip provides ergonomic advantages over other handle structures, such as those requiring an operator to grasp the handle as if grasping a writing instrument, for example. The operator may find the pistol grip easier to hold for long periods of time, easier to operate with one hand or easier to precisely manipulate the cutting blade assembly 8 to its desired target area, for example. However, these advantages are only provided for exemplary purposes, and the pistol grip may provide other advantages and conveniences.

As shown in FIGS. 2 and 5, the upper portion 32 extends approximately or generally parallel to the cutting blade assembly 8, while the lower portion 34 extends at an angle θ relative to the upper portion 32. The angle θ defined between the upper and lower portions 32 and 34 is less than 90° such that the lower portion 34 extends forward of the handle 2 and generally towards a surgical site in operation.

Orienting the lower portion 34 at the angle θ (less than 90°) relative to the upper portion 32 can provide advantages over other possible orientations. For example, this orientation reduces, minimizes or prevents interference between the lower portion 34 and a patient's chin during certain surgical procedures, such as sinus surgery. This orientation also enables at least one of a surgeon's fingers to be disposed at a position to facilitate manipulation of the collet assembly 36, which as is discussed in one of the succeeding sections, rotates a cutting window of the cutting blade assembly 8. However, these advantages are only provided for exemplary purposes, and this orientation can provide other advantages in sinus surgery or other applications.

As shown in FIGS. 4 and 5, a motor assembly 38 is disposed within the lower portion 34. The motor assembly 38 can be relatively heavy in comparison to other sub-elements of the handle 2. Disposing the relatively heavy motor assembly 38 in the lower portion lowers the disposition of weight of the handle 2 and thereby makes the handle 2 easier to hold since, for example, the relatively heavy lower portion 34 may be grasped between an operator's palm and one or more fingers.

However, disposing the motor assembly 38 within the lower portion 34 may provide other advantages over other dispositions. For example, this disposition enables the irrigation fluid and/or suction to travel along a relatively straight path through the handle 2 substantially or generally parallel to the cutting blade assembly 8. This relatively straight path can enhance regularity of fluid supply or suction, and/or reduce, minimize or prevent obstructions or blockages in the fluid supply or suction.

The motor assembly 38 can be disposed within a handle chassis 40, which in turn is disposed within a handle shell 42 of the lower portion 34. The handle shell 42 defines the exterior of the lower portion 34. The exterior of the upper portion is defined by a barrel 44.

The upper and lower portions 32 and 34 are secured together by handle fasteners 46 and internal fasteners 48. The handle and internal fasteners 46 and 48 communicate with apertures defined in the handle shell 42, handle chassis 40 and a bracket 50 of the barrel 44 to secure the upper and lower portions 32 and 34 together.

However, the handle and internal fasteners 46 and 48 are only provided for exemplary purposes, and the upper and lower portions 32 and 34 can be secured together in any manner. In fact, the upper and lower portions 32 and 34 do not even have to be separate elements and instead can be integral.

As shown in FIGS. 3-6, the irrigation fluid and suction are provided to extend through the barrel 44 and collet 36 of the handle 2. The irrigation fluid is supplied to the handle 2 via an irrigation fluid coupling 52 at a rear end of the barrel 44. The suction is supplied to the handle 2 via a suction coupling 54 adjacent and below the irrigation fluid coupling 52 at the rear end of the barrel 44.

The suction is provided within the handle 2 through a suction channel 56 defined in the suction coupling 54 and extends along a substantially straight path through the barrel 44 and collet 36 to the cutting blade assembly 8. The suction path extends generally along a central axis of barrel 44, collet 36 and cutting blade assembly 8.

The irrigation fluid is provided within the handle 2 through an irrigation fluid channel 58 which extends generally parallel to the suction channel 56 to a front section of the barrel 44, and then extends substantially transverse to the suction channel 56 along a transverse channel 60. The irrigation fluid then travels through the collet 36 substantially parallel to the suction channel 56 to the cutting blade assembly 8.

The handle signal line 14 is connected to the handle 2 via a cable assembly 62, which is then electrically connected to the motor assembly 38. The controller 6 can thereby send control signals to the motor assembly 38 via the handle signal line 14 and cable assembly 62 to actuate the motor on and off and to regulate the speed of the motor. However, the controller 6 can send and/or receive any other signals to or from the motor assembly 38 via the handle signal line 14 and cable assembly 62.

The cable assembly 62 is disposed at a rear end of the handle adjacent to and beneath the irrigation fluid coupling 52 and the suction coupling 54. Disposing the cable assembly 62 at this location enables the handle supply line 14, irrigation fluid supply tube 24 and suction supply tube 30 to extend from the rear end of the handle 2 substantially together and substantially parallel to each other as shown in FIG. 2. This disposition and direction of extension facilitates ease of operation of the handle 2 during surgery since the handle signal line 14, irrigation fluid supply tube 24 and suction supply tube 30 are collectively away from the surgical site. However, other advantages may be provided by this disposition and direction of extension, such as reducing, minimizing or preventing the line and tubes from becoming intertangled with each other and/or other lines, wires or tubes, for example.

Some or all of the sub-elements of the handle 2 can be made of lightweight materials, such as aluminum or ceramic, for example. Forming at least some of the sub-elements out of light weight materials reduces the overall weight of the handle 2 and thereby enhances its ease of operation.

The handle can include various other sub-elements. As shown in FIGS. 4-6, these sub-elements can include an irrigation dowel pin 64, rear seals 66 and 68, a rear shim 70, a tolerance ring 72, a gear shaft 74, a rear bearing 76, a front bearing 78, a front bearing holder 80, and front seals 82 and 84, for example.

To facilitate the manufacture of the handle with as few parts as possible, the irrigation supply bore may be drilled into the housing and the irrigation dowel pin 64 provides a means to close the irrigation supply hole to prevent unwanted leakage of irrigation fluid from the open end of the hole. The gear shaft 74 is mounted inside the handle 2 with its axis in line with the main axis of the handle and is supported on a front bearing 78 and rear bearing 76 such that it is free to rotate. A gear is formed as a part of the gear shaft, with gear teeth placed radially around the gear shaft. These gear teeth engage with the motor assembly 38 by means of a pinion gear mounted to the output shaft of the motor. In this particular implementation a face gear is used to provide for easier alignment of the motor assembly to the gear shaft where the pinion of the face gear may be a straight spur gear and its axial position relative to the gear shaft is not critical, provided that the faces of the spur teeth fully overlap the teeth on the gear. This means allows for easier assembly and alignment during manufacture.

The assembly of the motor assembly 38, gear shaft 74, front bearing 78 and rear bearing 76 form a mechanical transmission which may be designed to engage at any angle to suit the preference of the operator or the task. The transmission may utilize a lubricant material such as an oil or grease. Front seals 82 and 84 and rear seals 66 and 68 provide a means to prevent such lubricant from leaving the transmission and also to prevent the contamination of the transmission housing and gears by foreign material that may be present in the device during use or cleaning. The gears that form the transmission are optimally assembled in close contact to provide the best performance. One means of providing repeatable adjustment of such mechanical elements is the use of a shim 70 or shims to axially align the gear shaft 74 to the motor assembly 38. Once the correct shim size has been determined it may be used repeatedly to provide a consistent assembly location for the gear shaft into the housing 2.

The bearings 76 and 78 that are used to support the gear shaft are optimally mounted with precise concentricity in the housing 2 such that relative movement of the outer race of the bearings with respect to the housing 2 is prevented. One means to achieve such is to use an adhesive to bond the outer race of the bearing to the inner bore of the housing 2. Another preferred means to mount the bearings that may employed is the use of a tolerance ring 72 placed in to the housing 2. The tolerance ring 72 provides a means to maintain a tight fit between the outer race of the bearing and the inside diameter of the housing to prevent relative movement of the bearing outer race relative to the housing and further provides a means to repeatedly dis-assemble and re-assemble the bearing into the housing without damage to the bearing or housing or the necessity of removing adhesive.

III. Collet Assembly

Figure 7:
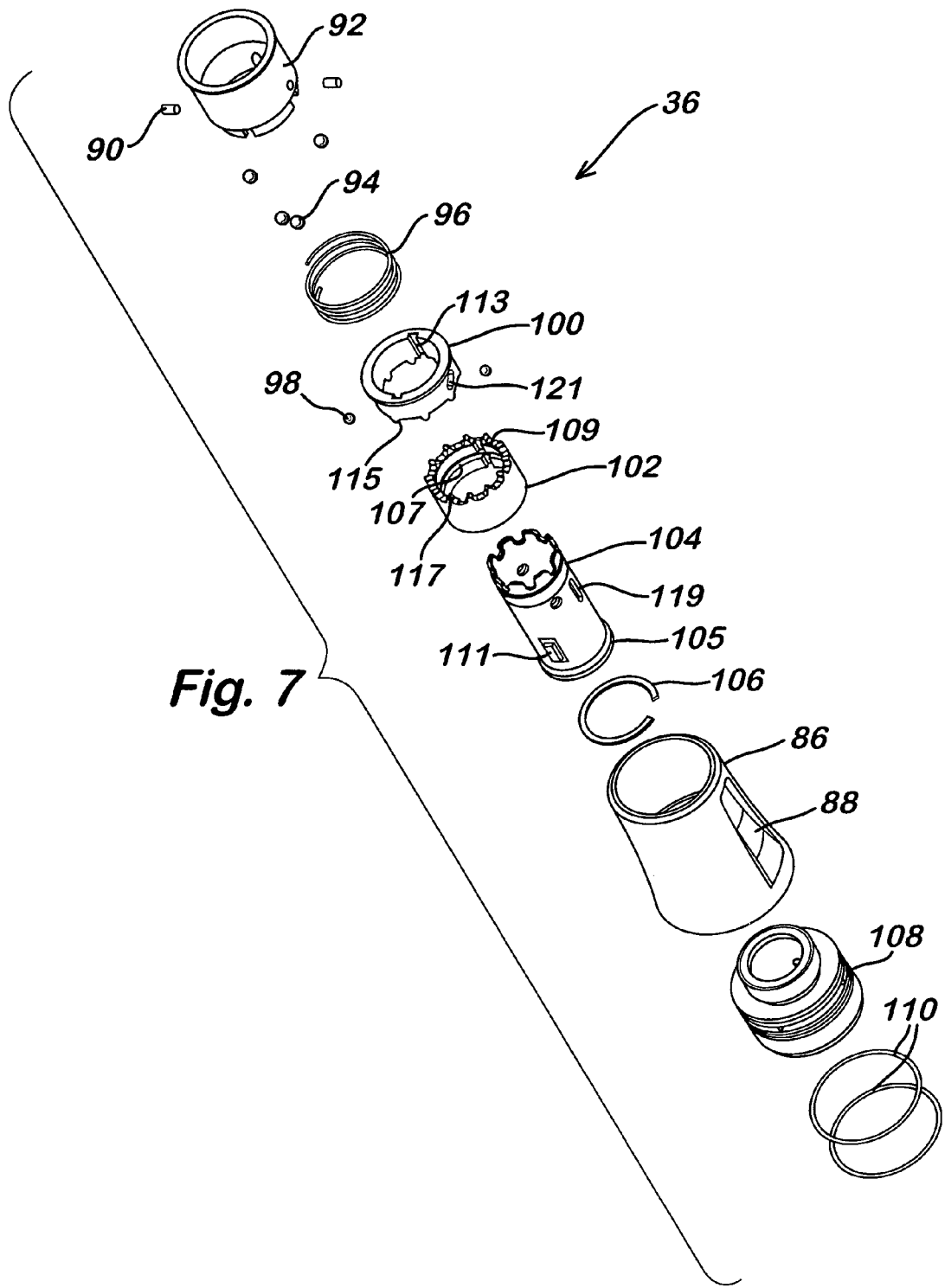
FIG. 7 is an exploded perspective view showing various sub-elements of the collet assembly 36.
Figure 8:
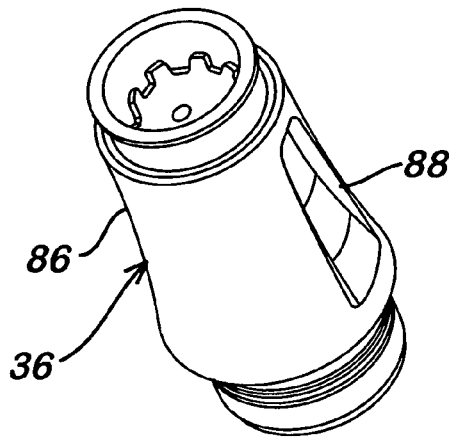
FIG. 8 is a perspective view showing the exterior of the collet assembly 36.
Figure 9:
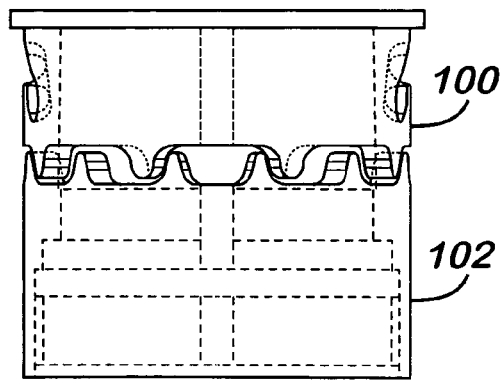
FIG. 9 is a front plan view showing various sub-elements of the collet assembly 36.

Various views of an exemplary embodiment of the collet assembly 36 are shown in FIGS. 7-9, wherein FIG. 7 is an exploded perspective view showing various sub-elements of the collet assembly 36, FIG. 8 is a perspective view showing the exterior of the collet assembly 36, and FIG. 9 is a front plan view showing some sub-elements of the collet assembly 36. An exemplary embodiment of the collet assembly 36 is described below in conjunction with FIGS. 7-9.

As shown in FIGS. 2 and 3, the collet assembly 36 is provided at the front end of the upper portion 32 of the handle 2. Disposing the collet assembly 36 at this location enables an operator, such as a surgeon, holding the handle 2 in a pistol grip manner, to touch and rotate the assembly collet 36 or a portion thereof with the tip of at least one of the surgeon's fingers. Rotating at least a portion of the collet assembly 36 in this manner enables the cutting window of the cutting blade assembly 8 to rotate, thereby orienting the direction of the shaving and/or cutting of the desired bodily material.

However, the orientation of the cutting window of the cutting blade assembly 8 does not need to be changed by rotating at least a portion of the collet assembly 36. Instead, the orientation of the cutting window of the cutting blade assembly 8 can be changed in accordance with any other method. For example, the orientation of the cutting window can be changed by moving the collet assembly 36, or one or more of the sub-elements thereof, in a linear direction. However, an exemplary embodiment is described below wherein rotation of at least a part of the collet assembly 36 changes the orientation of the cutting window.

As shown in FIGS. 7 and 8, the collet assembly 36 includes a swivel shell 86 that defines at least one gripping channel 88. The at least one gripping channel 88 enhances the surgeon's ability to grip the collet assembly 36 with the tip of at least one of the surgeon's fingers so as to rotate at least a part of the collet assembly 36. A single gripping channel 88 can be defined at the exterior of the swivel shell 86, or alternatively two or more gripping channels 88 can be provided to enhance ease of rotation or to address or accomplish any other purpose.

The swivel shell 86 does not have to include the at least one gripping channel 88. Instead, the swivel shell 86 can define a smooth exterior and not provide any method to enhance rotation of at least part of the collet assembly 36.

Alternatively, any other method of enhancing rotation of at least part of the collet assembly 36 can be provided. For example, the exterior of the swivel shell 86 can define a rough exterior to enhance gripping ability. Alternatively, the exterior of the swivel shell 86 can define ridges, bumps or any other projections to enhance gripping ability, for example.

The collet assembly 36 can be provided such that only a portion of the collet assembly 36 is rotatable to enable the orientation of the cutting window of the cutting blade assembly 8 to be changed while an inner blade of the cutting blade assembly 8 rotates. For example, the swivel shell 86 can be mechanically separated from the outer hub of the cutting blade assembly 8 so that in the event of a jam the swivel shell 86 does not rotate. However, the collet assembly 36 can also be provided so that the entire assembly is rotatable.

Although the invention is intended to cover any method to perform this operation, FIGS. 7 and 9 show a combination of sub-elements that enable manual rotation of the swivel shell 86 to change the orientation of the cutting window while the inner blade of the cutting blade assembly 8 rotates. As shown in FIGS. 7 and 9, the collet assembly can include release pins 90, a release ring 92, retention balls 94, a lock spring 96, unlocking balls 98, a sliding cam 100, a stationary cam 102, a retention sleeve 104, a retaining clip 106, the swivel shell 86, a base mount 108, and base mount seals 110. These sub-elements are also shown in their assembled state in FIGS. 5 and 6.

The collet assembly can include a stationary cam 102 which is attached to the base mount 108 such that an interior gap defines a location for the retention of a flange 105 on the proximal end of the retention sleeve 104, thus capturing the retention sleeve 104 and preventing it from moving axially, but allowing it to rotate freely and concentrically with respect to the main axis of the collet assembly 36. One method of capturing the flange 105 on the retention sleeve 104 is to use a retaining clip 106 which fits into an internal groove 107 in the stationary cam 102 and defines a gap which ensures that rotation is free, but that axial movement is restricted. The use of the retaining clip 106 further facilitates the assembly of the mechanism, by allowing the base mount 108 to be assembled into contact with the retaining clip 106 thereby setting the relative position of the base mount 108 to the stationary cam 102 and eliminating the need to manually adjust this engagement.

Two interior grooves 109 are located on the stationary cam 102 to provide relief to allow the stationary cam 102 to slide over two keys 111 on the exterior of the retention sleeve 104. These two grooves are provided as a means to aid assembly and are not functional once the collet assembly 36 has been completed. The sliding cam 100 also has two interior grooves 113 which engage with the keys 111 on the exterior of the retention sleeve 104 preventing relative rotational motion of these parts, but allowing the sliding cam 100 to slide freely in an axial direction along the length of the retention sleeve 104. This engagement is the means by which rotational motion is transmitted between the sliding cam 100 and the retention sleeve 104 and subsequently to the blade hub when the swivel shell 86 is rotated. The sliding cam 100 engages with the stationary cam 102 by means of teeth 115 and 117 that are located on the faces of each part facing towards each other. The teeth 115 and 117 are held in engagement by the spring 96 which is in turn retained by the release ring 92 which is retained by the release pins 90 which are engaged in holes in the release ring 90 and whose ends are placed in slots 119 in the retention sleeve 104. The release pins 90 are retained by the assembly of the swivel shell 86 which prevents the pins from falling out the holes which capture them in the release ring 92.

The teeth 115 and 117 on the cams 100 and 102 that engage with each other have geometry which when urged into engagement by the lock spring 96, are not permitted to slide against each other by means of friction. In order to prevent sliding of the teeth against other the contact angle of the teeth 115 and 117 is substantially less than 45 degrees and in this case is 15 degrees. The contact angle can be adjusted to be as low as zero degrees or even to an negative angle if desired to further prevent the possibility of sliding of the cam teeth 115 and 117, however reduction of the angle to near zero degrees has the undesirable effect of introducing backlash between the teeth which would correspond to backlash in the retention of the blade hub. In the optimal implementation, an angle is chosen that provides for strong retention and no sliding, whilst minimizing or eliminating backlash between the teeth 115 and 117. An angle of 15 degrees for example permits excellent retention of the teeth 115 and 117 with respect to each other and also permits the lock spring 96 to push the angled teeth into engagement with each other eliminating virtually all backlash from the tooth engagement.

The grooves 121 on the exterior of the sliding cam 100 are shaped with a V profile and receive the unlocking balls 98 which engage in pockets inside the swivel shell 86. The balls 98 slide in the V shaped grooves 121 in the sliding cam 100 when the swivel shell 86 is rotated. The angle of the V shaped groove 121 is important to facilitate the optimal feel of the swivel in surgeons fingers. If the V groove 121 is too steep with an included angle of much less that 90 degrees, the friction will prevent easy sliding of the balls 98 in the V groove 121 and the swivel will not rotate and lift the sliding cam 100 up. Conversely if the included angle of the V groove 121 is too shallow, substantially greater than 90 degrees then the unlocking balls 98 will slide easily but the surgeons fingers will be required to rotate the swivel shell 86 a large degree of rotation before the sliding cam 100 has been lifted out of engagement with the stationary cam 102, thereby giving a loose feel to the swivel assembly. Optimally, an angle of approximately 90 degrees gives a good feel to the surgeon and allows the unlocking balls 98 to lift the sliding cam up without significant frictional resistance.

Rotation of the swivel shell 86 by the surgeon causes a corresponding rotation of the sliding cam 100, lifting the sliding cam 100 out of engagement with the stationary cam 102. Once the sliding cam 100 is free from the stationary cam 102, it can cause a corresponding rotation of the retention sleeve 104. In this way, a rotation of the swivel shell 86 causes a reorientation of the cutting window in the cutting blade assembly 8, via retention sleeve 104. However, should the retention sleeve 104 be urged to rotate, for example by the cutting blade assembly 8 becoming jammed, the rotation will be prevented by the engagement of the sliding cam 100 in the stationary cam 102. The action of the swivel shell 86 to lift the sliding cam 100 out of engagement with the stationary cam 102 means that while a rotation of the swivel shell will cause a corresponding rotation of the retention sleeve 104, the reverse will not be permitted (i.e. an attempt to rotate the retention sleeve 104 will not cause a corresponding rotation of the swivel shell 86). This provides the assurance that in the event of a jam the swivel shell will be prevented from rotating, thereby avoiding the possibility of injury to the surgeon.

As well as providing a rotation for the cutting window of the cutting blade assembly, the collet assembly also provides a mechanism for the removal and replacement of the cutting blade assembly. The blade hub has a number of radially disposed dimples 144 which are engaged by the retention balls 94. The retention balls are held into engagement with the blade hub by an angled surface on the interior of the release ring 92 which functions as a wedge. The wedge is held into engagement with the retention balls by the lock spring and further the lock spring forces the wedge to press on the retention balls pushing them radially inward and in to contact with the blade hub with a force substantially greater than the axial force of the lock spring due to the shallow angle of the wedge surface on the interior of the release ring 92.

n order to unlock the blade hub from engagement with the retention balls, the surgeon or nurse presses the release ring in a proximal direction, compressing the lock spring 96 and sliding the wedge surface away from contact with the retention balls. Once the release ring has been depressed, the blade may be retracted from the collet assembly and as it is retracted, the shallow angle of the dimples pushes the retention balls radially outward such that they no longer engage the dimples and permit the blade hub to be removed. During storage when no blade hub is present in the collet assembly, the spring pushes on the proximal end of the release ring and moves it in a distal direction. To prevent long term pressure on the retention balls by the wedge, the release pins 90 may be made to contact the end of the slots in the retention sleeve, such that pressure on the balls is relieved at the end of the travel. This may be desirable to discourage the retention balls from sticking in the pockets provided in the retention sleeve.

IV. Tube Connector

Figure 10:
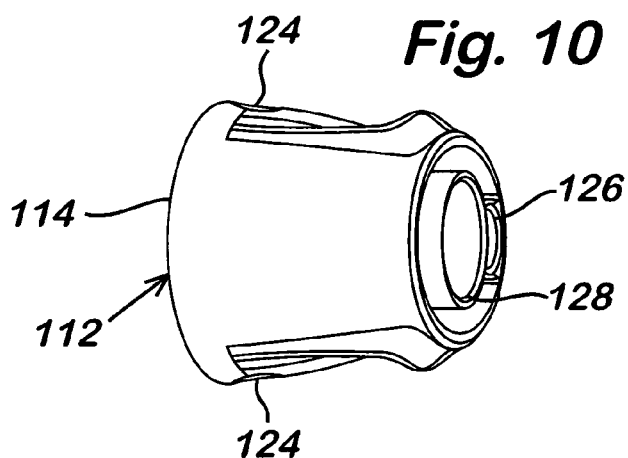
FIG. 10 is a perspective view showing the exterior of the tube connector 112.
Figure 11:
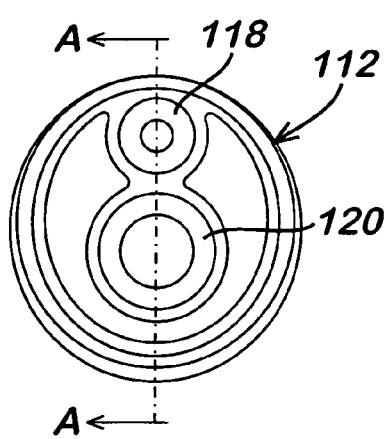
FIG. 11 is a plan view of the tube connector 112.
Figure 12:
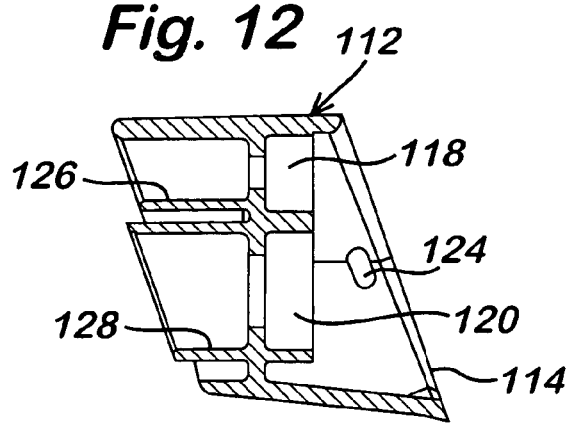
FIG. 12 is a side sectional view of the tube connector 112 taken along plane A-A of FIG. 11.

Various views of an exemplary embodiment of the tube connector are shown in FIGS. 10-12, wherein FIG. 10 is a perspective view showing the exterior of the tube connector 112, FIG. 11 is a rear plan view of the tube connector 112, and FIG. 12 is a side sectional view of the tube connector 112 taken along plane A-A of FIG. 11. An exemplary embodiment of the tube connector 112 is described below in conjunction with FIGS. 10-12.

The tube connector 112 shown in FIGS. 10-12 is connected to a rear end of the barrel 44 shown in FIGS. 3 and 4. Specifically, when connected, surface 114 of the tube connector 112 abuts against, or is disposed adjacent to, surface 116 of the barrel 114, such that the irrigation fluid coupling 52 of the barrel 44 extends within irrigation fluid entry channel 118, and the suction coupling 54 extends within suction entry channel 120.

The irrigation fluid coupling 52 and the suction coupling 54 can be formed of an elastic or substantially elastic material, such as rubber, for example, so as to provide a leak-proof or substantially leak-proof fitting within the irrigation fluid entry channel 118 and the suction entry channel 120. However, any method can be used to provide a leak-proof or substantially leak-proof fitting between these elements. For example, the irrigation fluid entry channel 118 and the suction entry channel 120 can be formed of an elastic or substantially elastic material, such as rubber, for example, in addition to, or instead of, the irrigation fluid coupling 52 and the suction coupling 54. Most preferably, the irrigation fluid coupling 52 and the suction coupling 54 are formed from a rigid material such as aluminum, and rubber O-rings are inserted in channels 118 and 120 to provide a leak-proof fitting. All of these fitting methods provide the advantage of enabling the couplings 52 and 54 to be easily and quickly removed from the channels 118 and 120.

However, the couplings 52 and 54 can be permanently or semi-permanently fixed to the channels 118 and 120. For example, the irrigation fluid coupling 52 and the suction coupling 54 can be bonded to either interior or exterior walls that define the irrigation fluid entry channel 118 and the suction entry channel 120 by any other method, such as by glue, epoxy, press fitting, melting, or welding, for example.

Similarly, the tube connector 112 can be secured to the barrel 44 by any method. For example, as shown in the exemplary embodiment of FIGS. 4, 10 and 12, one or more detents 122 disposed on a periphery of the barrel 44 snap into, or are otherwise engaged with, corresponding apertures 124 defined in the tube connector 112. However, any other method can be used to secure the tube connector 112 to the barrel, such as providing the tube connector 112 with detents that snap into, or are otherwise engaged with, corresponding apertures defined in the barrel 44. Both of these methods provide the advantage of enabling the tube connector 112 to be easily and quickly removed from the barrel 44.

However, the tube connector 112 can be permanently or semi-permanently secured to the barrel 44. For example, the tube connector 112 can be secured to the barrel 44 by any other method, such as by glue, epoxy, press fitting, melting, or welding, for example.

Regardless of the attachment method between the tube connector 112 and the barrel 44, either or both of these elements can be keyed to the other. Providing this structure reduces, minimizes or prevents the tube connector 112 from turning relative to the handle 2, which is especially likely to occur when the irrigation fluid supply tube 24 and the suction supply tube 30 are being connected to the tube connector 112, which is described below.

The tube connector 112 defines an irrigation fluid projection 126 and a suction projection 128. The projections 126 and 128 are formed to be an appropriate size such that the irrigation fluid supply tube 24 can snugly fit inside the irrigation fluid projection 126, and the suction supply tube 30 can snugly fit inside the suction projection 128 and are glued in position so as to provide leak-proof or substantially leak-proof fittings. However, any other method of attachment can be provided between these elements, including push fit attachments which allow the irrigation fluid supply tube and the suction supply tube to be disconnected from the irrigation fluid projection 126 and the suction projection 128.

The correct orientation of the tube connector 112 is ensured by the angled surface 114, and by the different sizes of the couplings 52 and 54. The size of the irrigation fluid coupling 52 matches the size of the irrigation fluid entry channel 118, but not that of the suction entry channel 120. Similarly the size of the suction coupling 54 matches the size of the suction entry channel 120, but not that of the irrigation fluid entry channel 118. Thus the tube connector can be attached to the handpiece in one orientation only. Additionally, the angled surface 114 on the tube connector 112 matches the angled surface 116 on the barrel 44 of the handpiece, again preventing attachment of the tube connector in an incorrect orientation.

The tube connector 112 enables the irrigation fluid supply tube 24 and the suction supply tube 30 to be connected to the rear end of the handle 2. Thus, the irrigation fluid supply tube 24 and/or the suction supply tube 30 are not directly connected to the cutting blade assembly 8. This structure provides an advantage of enabling the cutting blade assembly 8 or a part thereof to be changed without requiring that the irrigation fluid supply tube 24 and/or the suction supply tube 30 be disconnected from the handle 2, which enhances operation of the apparatus 1. This feature is especially advantageous in surgical procedures that require the cutting blade assembly 8 or a part thereof to be changed during the surgical procedure or operation, such as in sinus surgery which may require the use of more than one blade during a single operation or procedure.

V. Cutting Blade Assembly

Figure 13:
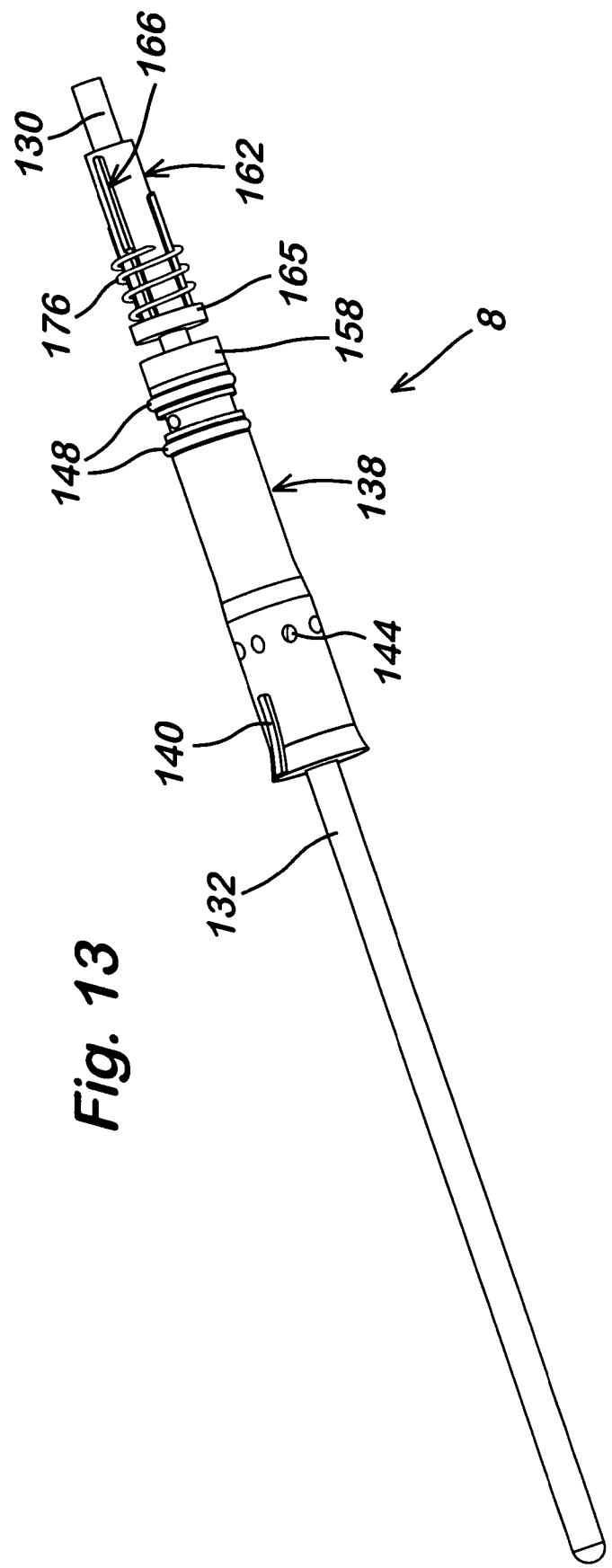
FIG. 13 is a perspective view showing the exterior of the cutting blade assembly 8.
Figure 16:
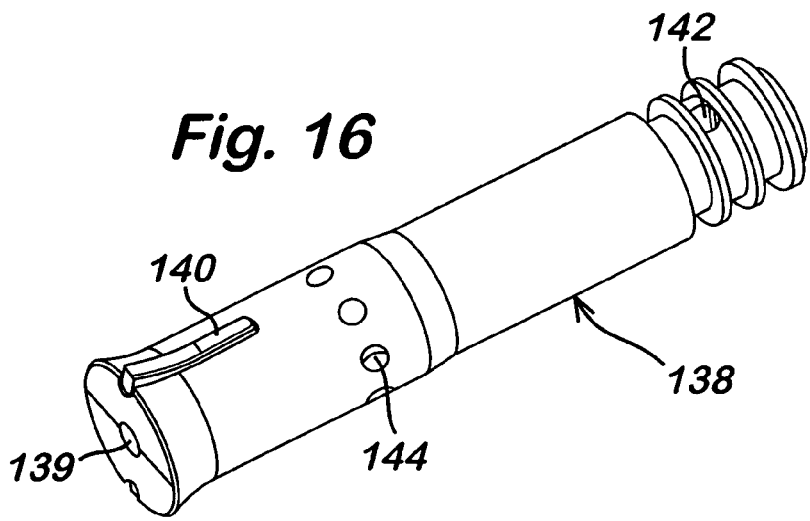
FIG. 16 is a perspective view of the outer hub 138 of the cutting blade assembly 8.
Figure 17:
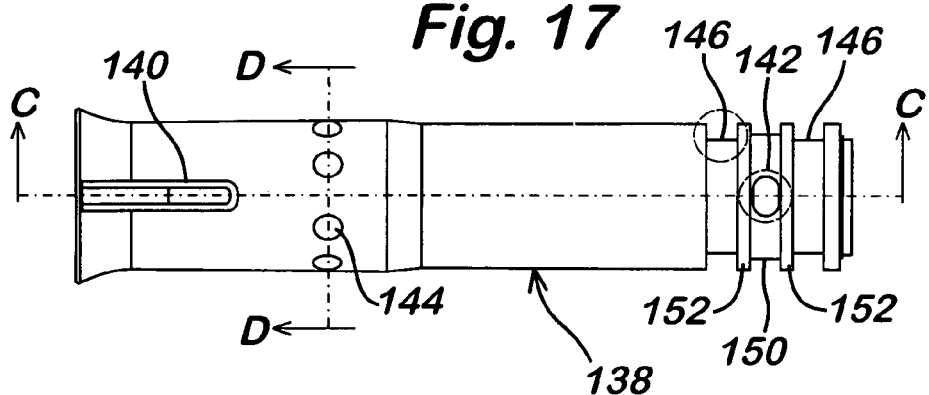
FIG. 17 is side plan view of the outer hub 138 shown in FIG. 16.
Figure 18:
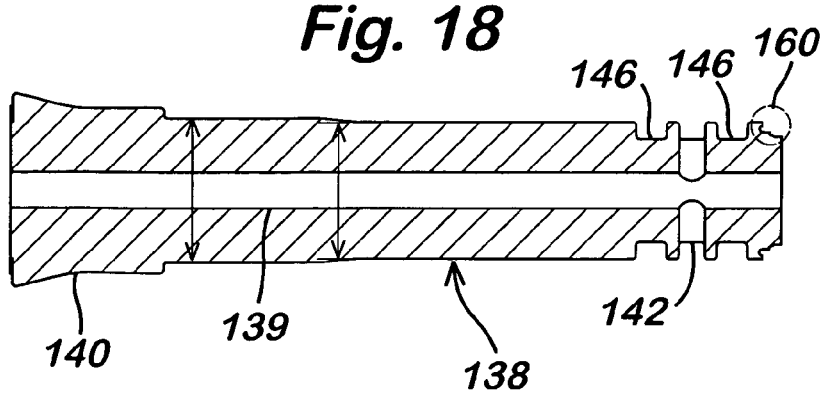
FIG. 18 is a sectional view of the outer hub 138 taken along plane C-C of FIG. 17.
Figure 19:
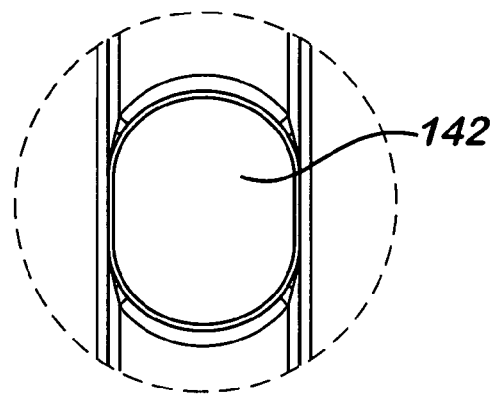
FIG. 19 is a side plan view of an irrigation hole 142 defined in the outer hub 138 shown in FIG. 17.
Figure 20:
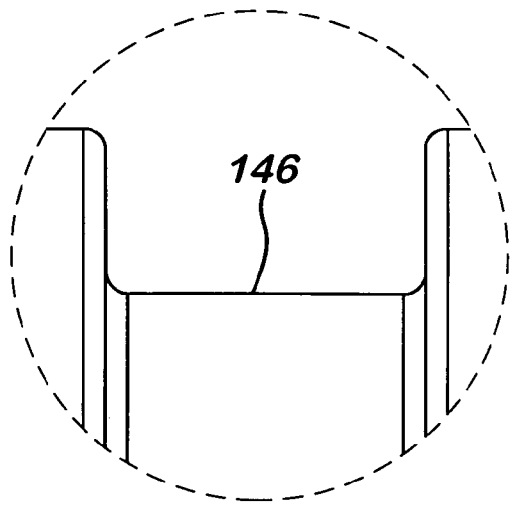
FIG. 20 is a side plan view of a portion of the outer hub 38 defining retention channels 146 shown in FIG. 17.
Figure 21:
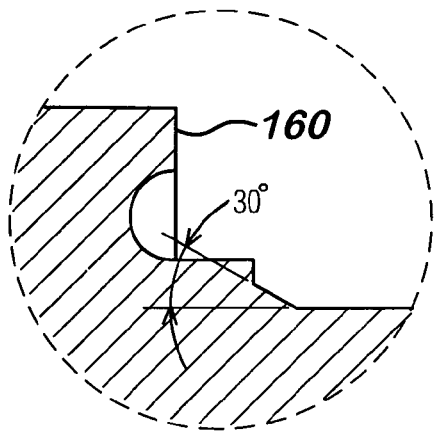
FIG. 21 is a sectional view of a portion of the outer hub 138 defining the proximal end 160 shown in FIG. 18.
Figure 22:
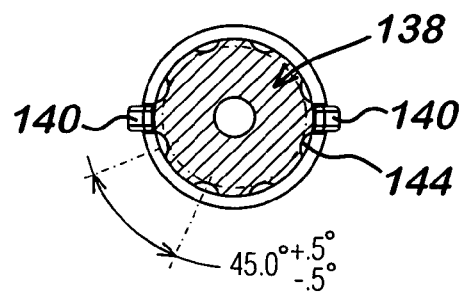
FIG. 22 is a sectional view of the outer hub 138 taken along plane D-D of FIG. 17.
Figure 23:
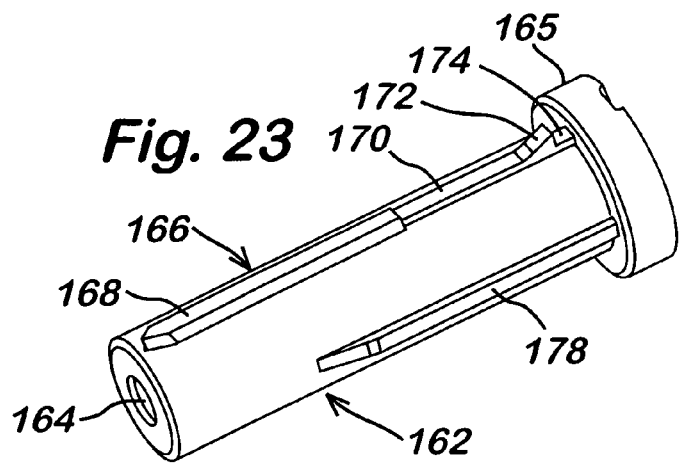
FIG. 23 is a perspective view of the inner hub 162 of the cutting blade assembly 8.
Figure 24:
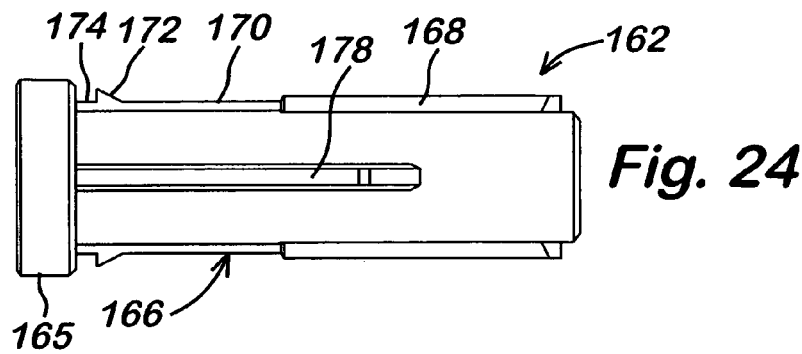
FIG. 24 is a side plan view of the inner hub 162 shown in FIG. 23.
Figure 25:
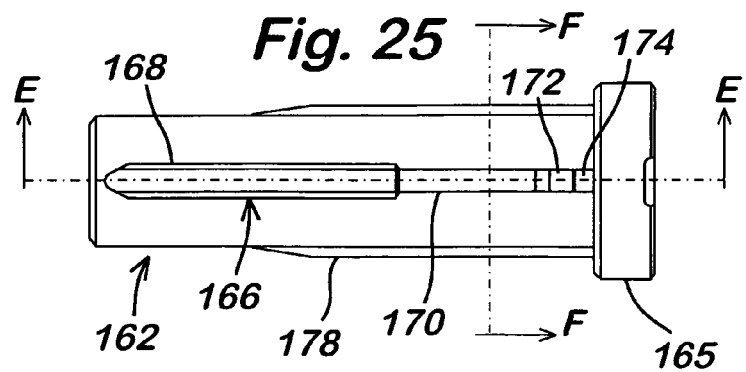
FIG. 25 is another side plan view of the inner hub 162 that is rotated 90° relative to the view of FIG. 24.
Figure 26:
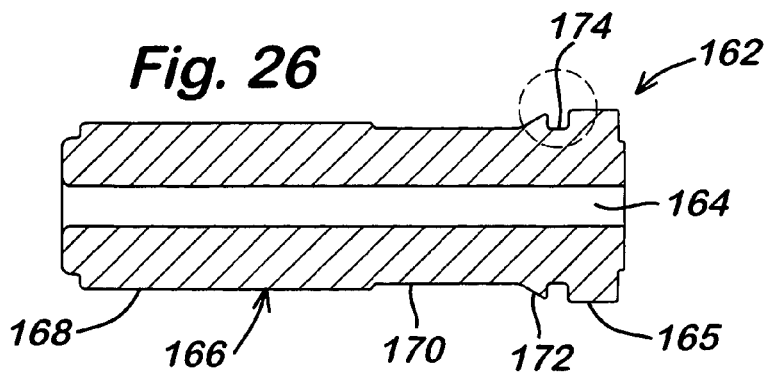
FIG. 26 is a sectional view of the inner hub 162 taken along plane E-E of FIG. 25.

Various views of an exemplary embodiment of the cutting blade assembly 8 are shown in FIGS. 13-28, wherein FIG. 13 is a perspective view showing the exterior of the cutting blade assembly 8; FIG. 14 is a partial perspective view showing a portion of the exterior of the cutting blade assembly 8; FIG. 15 is a sectional view of the cutting blade assembly 8 taken along plane B-B of FIG. 14; FIG. 16 is a perspective view of the outer hub 138 of the cutting blade assembly 8; FIG. 17 is side plan view of the outer hub 138 shown in FIG. 16; FIG. 18 is a sectional view of the outer hub 138 taken along plane C-C of FIG. 17; FIG. 19 is a side plan view of an irrigation hole 142 defined in the outer hub 138 shown in FIG. 17; FIG. 20 is a side plan view of a portion of the outer hub 38 defining retention channels 146 shown in FIG. 17; FIG. 21 is a sectional view of a portion of the outer hub 138 defining the proximal end 160 shown in FIG. 18; FIG. 22 is a sectional view of the outer hub 138 taken along plane D-D of FIG. 17; FIG. 23 is a perspective view of the inner hub 162 of the cutting blade assembly 8; FIG. 24 is a side plan view of the inner hub 162 shown in FIG. 23; FIG. 25 is another side plan view of the inner hub 162 that is rotated 90° relative to the view of FIG. 24; and FIG. 26 is a sectional view of the inner hub 162 taken along plane E-E of FIG. 25. An exemplary embodiment of the cutting blade assembly 8 is described below in conjunction with FIGS. 13-28.

The cutting blade assembly 8 in accordance with the invention can be used to shave, cut and/or remove bodily tissue from a surgical site. The invention is intended to cover any structure that can accomplish this and/or other operations.

For convenience of explanation, FIG. 13 depicts a cutting blade assembly 8 that includes a straight blade structure. However, any other blade structure can be used, such as a bent blade structure, for example, that may provide other advantages, such as providing access to bodily tissue that would be difficult or impossible to reach via a straight blade structure, for example.

A blade structure can be used that defines a knife edge with a substantially uniform cutting surface at and/or adjacent to its distal end. Alternatively, other cutting surfaces can be used, such as a cutting surface that defines one or more cutting teeth, for example. In fact, the blade structure does not even have to define a sharp cutting surface, and instead can define another structure, such as a burr, for example, that may provide other advantages, such as facilitating the shaving and/or cutting of muscle and/or bone, for example.

The cutting blade structure of the cutting blade assembly 8 can be manufactured from rigid material, such as stainless steel, for example. However, the cutting blade can be manufactured from other materials, such as elastic and/or bendable materials for example, that may provide advantages over rigid materials, such as providing enhanced access to certain surgical sites, for example. One common arrangement is to provide a flexible shaft, typically of a mesh or wound spring construction, covered by a sealing sleeve.

For convenience of explanation, an exemplary embodiment is described below that includes a rotating cutting surface. However, any other type of cutting surface can be provided, such as a cutting surface that is linearly movable.

All or part of the cutting blade assembly 8 can be provided as sterile, and can be sterilized using ethylene oxide gas (EO), for example. All or part of the cutting blade assembly can be placed in a protective tray, that is heat sealed inside a Tyvek® and ionomer pouch, which in turn is placed inside of a paperboard carton and shrink-wrapped.

As shown in FIGS. 13-15, the cutting blade assembly 8 includes an inner tube 130 that extends within an outer tube 132. A gap 134 is defined between the inner and outer tubes 130 and 132. Both the inner and outer tubes 130 and 132 are hollow, such that a distal suction channel 136 is defined within the inner tube 132.

The distal suction channel 136 communicates with the suction channel 56 shown in FIG. 5. Thus, in operation, bodily material and/or irrigation fluid can be removed from the surgical site by suction provided to the surgical site via the suction source 28, the suction supply tube 30, the suction channel 56 and the distal suction channel 136.

As shown in FIGS. 5 and 15, the distal suction channel 136 and the suction channel 56 generally extend through a central portion of each of the cutting blade assembly 8 and the upper portion 32 of the handle 2. In fact, in the exemplary embodiment shown in FIGS. 5 and 15, the distal suction channel 136 and the suction channel 56 are generally co-axial with the cutting blade assembly 8 and the upper portion 32 of the handle 2. This enables the bodily material and/or irrigation fluid to be removed along a generally straight path which enhances operation, minimizes or reduces, prevents blockages between the surgical site and the suction source 28.

However, the invention is intended to cover other methods and structures to remove the bodily material and/or irrigation fluid from the surgical site. For example, the distal suction channel 136 and the suction channel 56 do not have to be co-axial with the cutting blade assembly 8 and the upper portion 32 of the handle 2. In fact, the distal suction channel 136 and the suction channel 56 do not even have to define a straight or substantially straight path between the surgical site and the suction supply tube 30.

The gap 134 that is defined between the inner and outer tubes 130 and 132 communicates with the transverse channel 60 and the irrigation fluid channel 58 of the barrel 44 shown in FIG. 5. This communication, which is discussed in more detail below with regard to other sub-elements of the cutting blade assembly 8, enables irrigation fluid to be supplied to the cutting surface and/or the surgical site via the irrigation fluid source 22 and the irrigation fluid supply tube 24.

Defining and utilizing the gap 134 between the inner and outer tubes 130 and 132 provides a convenient and simple structure to supply irrigation fluid to the cutting surface and/or the surgical site. However, the invention is intended to cover other structures and methods of supplying irrigation fluid to the cutting surface and/or the surgical site. In fact, the invention is intended to cover an apparatus that does not even utilize irrigation fluid.

The distal end of the inner tube 130 defines a cutting surface. The distal end of the outer tube 132 defines a cutting window, such as an opening, to expose the cutting surface of the inner tube 130 to the bodily tissue to be shaved, cut and/or removed. The cutting window can define any sized opening, such as an opening that extends along approximately half of the cross-sectional area of the outer tube 132, for example. A cutting opening of this size provides an advantage of enabling a surgeon to expose a significant amount of bodily tissue to the cutting surface of the inner tube 130 while also shielding other tissue that is not to be cut, shaved and/or removed.

As previously discussed, the cutting surface of the inner tube 130 can define a sharp uniform or substantially uniform edge or can have any other appropriate shape, such as a shape defining one or more teeth, for example. Further, the walls of the outer tube 132 that define the cutting window can cooperate with the cutting surface of the inner tube 130. For example, the outer tube 132 walls can define sharp uniform or substantially uniform edges, or can have any other appropriate shape, such as a shape defining one or more teeth which, in one exemplary embodiment, may cooperate with teeth of the cutting surface of the inner tube 130.

In operation, in an exemplary embodiment of the invention, the inner tube 130 is rotated such that its cutting surface contacts and thereby cuts and/or shaves bodily tissue via the cutting window of the outer tube 132. The inner tube 130 is rotated via the motor assembly 38 shown in FIG. 4. The motor assembly 38 can rotate the inner tube 130 at any rotational speed, such as up to 44,000 rpm, for example. The communication between the inner tube 130 and the motor assembly 38 is discussed previously in detail with regard to other sub-elements of the cutting blade assembly 8.

The outer tube 132 is isolated from the inner tube 130 such that the outer tube 132 does not rotate with the inner tube 130. However, the outer tube 132 can be manually rotated by the surgeon via the collet assembly 36 so as to reorient the cutting window. The communication between the collet assembly 36 and the outer tube 132 as well as its isolation from the inner blade 130 is discussed in detail previously with regard to other sub-elements of the cutting blade assembly 8.

The cutting blade assembly also includes an outer hub 138. The outer tube 132 extends partially through a longitudinal channel 139, which is defined in the outer hub 138 and shown in FIGS. 16 and 18. An exemplary embodiment of the outer hub 138 is more fully shown in FIGS. 13-15 with other sub-elements of the cutting blade assembly 8, while FIGS. 16-22 exclusively shown the outer hub 138 and sub-elements thereof.

The outer tube 132 is secured to an interior surface of the outer hub 138 at a location such that the proximal end of the outer tube 132 is distal to a through hole 142, which extends through the outer hub 132 transverse to the longitudinal channel 139. Thus, the outer tube 132 does not extend entirely through the outer hub 138. These elements can be secured together by any method, such as by overmolding, glue, epoxy, press fitting, or welding, for example.

The outer hub 138 is received within a longitudinal channel defined within the collet assembly 36. Specifically, the proximal end of the outer hub 138 is flared and defines flared guides 140 that communicate with corresponding grooves defined in the interior surface of the collet assembly 36. Further, the exterior of the outer hub 138 defines dimples 144 that communicate with retention balls 94, which are shown in FIG. 7 and disposed inside of the collet assembly 36. In particular, the retention balls 94 are disposed in the dimples 144 and apply a pressing force between an interior surface of the collet assembly 36 and an exterior surface of the outer hub 138 in a direction transverse to longitudinal axis of these elements. As shown in FIG. 22, the dimples 144 are substantially uniformly defined around a circumference of the outer hub 138, and are spaced apart from each other at angles of approximately 45°. Disposing the dimples 144 around the circumference of the outer hub 138 provides an advantage of enabling a substantially uniformly distributed pressing force to be applied around the circumference of the outer hub 138. However, any number of one or more dimples 144 and retention balls 94 can be used. Further, if multiple dimples 144 and retention balls 94 are used, the dimples 144 can be spaced apart from each other by any distance.

The exemplary embodiment shown in the figures provides the dimples 144 at substantially the same longitudinal position around the periphery of the outer hub 138. However, the dimples can be provided at different longitudinal positions along the periphery of the outer hub 138.

The communication between the above structures enables the outer hub 138 to remain substantially static relative to the collet assembly 36, and in particular enables rotation of the collet assembly 36 to cause a corresponding rotation of the outer hub 138. Further, since the outer tube 132 is secured to the outer hub 138, rotation of the collet assembly 36 causes a corresponding rotation of the outer tube 132, which enables a surgeon to reorient the cutting window.

The communication between the dimples 144 and the retention balls 94 is advantages in that it provides a rather uniformly distributed transverse pressure over a relatively large surface area of the collet assembly 36 and the outer hub 138. However, other structures can be used to retain the outer hub 138 within the collet assembly 36. For example, the exterior of the outer hub 138 can define grooves to communicate with a corresponding structure to provide a pressure fitting between the outer hub 138 and the collet assembly 36.

As shown in FIGS. 17 and 20, the exterior of the outer hub 138 defines retention channels 146 on opposing sides of the through hole 142. As shown in FIGS. 13-15, static O-rings 148 are disposed and held within the retention channels 146. A through hole channel 150 is defined by the exterior of the outer hub 138 at substantially the same longitudinal position as the through hole 142. A pair of ribs 152 separate the retention channels 146 and corresponding O-rings 148 from the through hole 142 and the through hole channel 150.

When the outer hub 138 is disposed within the collet assembly 36, the through hole 142 and the through hole channel 150 are disposed at substantially the same longitudinal position as the transverse channel 60 defined in the barrel 44. Thus, irrigation fluid flowing distally along the irrigation fluid channel 58 and the transverse channel 60 enters the through hole channel 150 and the through hole 142. The irrigation fluid then travels distally along the exterior of the inner tube 130 and the gap 134 defined between the inner and outer tubes 132 and 134 to the cutting window of the outer tube 132.

The irrigation fluid entering the through hole channel 150 is prevented or substantially prevented from leaking out and traveling longitudinally along the exterior of the outer hub 138 by the static O-rings 148. However, the static O-rings 148 do not have to be used, and any other structure can be provided to prevent or substantially prevent the irrigation fluid from leaking out of the through hole channel 150 and traveling longitudinally along the exterior of the outer hub 138.

As shown in FIG. 15, a dynamic O-ring 154 is disposed at a proximal end of the outer hub 138. The dynamic O-ring 154 seals the proximal end of the gap 156 defined between the exterior surface of the inner tube 130 and the interior surface of the outer hub 138. This seal prevents or substantially prevents irrigation fluid that has passed down the through hole 142 from traveling proximally along the exterior of the inner blade 130 beyond the proximal end of the outer hub 138.

The dynamic O-ring 154 is held in place by a donut 158 that is secured to the proximal end 160 of the outer hub 138. The donut 158 can be secured to the proximal end of the outer hub 138 by any method, such as by ultrasonic welding. As shown in FIG. 21, the proximal end 160 can be shaped to enhance acceptance of the donut 158 by ultrasonic welding. However, any other method can be used to secure the donut 158 in place, such as with glue, epoxy, or press fitting, for example.

Figure 27:
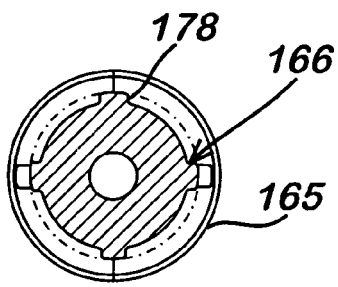
FIG. 27 is a sectional view of the inner hub 162 taken along plane F-F of FIG. 25.

The cutting blade assembly 8 also includes an inner hub 162. The inner tube 130 extends entirely through a longitudinal channel 164, which is defined in the inner hub 162 and shown in FIGS. 23 and 26. An exemplary embodiment of the inner hub 162 is more fully shown in FIGS. 23-26, and sub-elements of the inner hub 162 are shown in FIGS. 27 and 27.

The inner tube 130 is secured to an interior surface of the inner hub 162, such that proximal end of the inner tube 130 extends beyond the proximal end of the inner hub 162, and the distal end of the inner tube 130 is distal to the distal end of the inner hub 162. These elements can be secured together by any method, such as by overmolding, glue, epoxy, press fitting, or welding, for example. Extending the proximal end of the inner tube 130 beyond the proximal end of the inner hub 162 can provide various advantages. For example, the structure enables the material traveling in a proximal direction through the distal suction channel 136 via suction to pass in an unobstructed manner through the inner hub 162, thereby enhancing the cleanability of the apparatus.

The inner hub 162 is received within a longitudinal channel defined within the collet assembly 36 and the barrel 44. Structures that enable the inner hub 162 to be received and held within the collet assembly 36 and the barrel 44 are discussed below.

Figure 28:
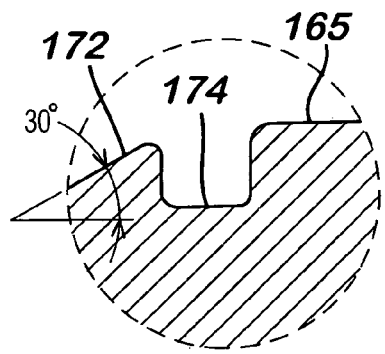
FIG. 28 is a sectional view of a portion of the inner hub 162 defining the spring retention channels 174 shown in FIG. 26.

As shown in FIGS. 23-27, the exterior of the inner hub 162 defines an annular hub 165 at its distal end, and a pair of first ribs 166 that extend longitudinally along the inner hub 162. The first ribs 166 include drive splines 168 that extend from a position approximately adjacent the proximal end of the inner hub 162 to approximately the longitudinal midpoint of the inner hub 162. The first ribs 166 also include spring retention sections 170 that extend from the distal end of the drive splines 168 to the annular hub 165. Spring retention projections 172 are defined on the spring retention sections 170 adjacent and spaced from the annular hub 165 so as to define spring retention channels 174 therebetween, an enlarged view of which is shown in FIG. 28.

A spring 176, shown in FIGS. 13-15, is retained along the spring retention sections 170. Specifically, a distal end of the spring 176 is held in the spring retention channels 174 between the spring retention projections 172 and the annular hub 165. The spring retention projections 172 can be tapered to facilitate insertion of the spring 176. The distal end of the drive splines 168 can also serve to hold the proximal end of the spring within the spring retention sections 170.

The spring 176 provides axial pressure on the inner hub 162 helping to guarantee good contact between the bearing surfaces at the distal end of the shaver blades. In the case of burrs, the same function is performed, but the bearing surface with the pair of washers. The axial force is applied as the blade is engaged. The proximal end of the spring 176 comes into contact with a shoulder machined into the drive shaft. The purpose of this shoulder is to be a positive location for initiating compression of the spring 176. The spring 176 can be compressed 100% in extreme cases with no detrimental effects. In this case, the annular hub 165 of the inner hub 162 will eventually contact the shaft or the distal end of the solid height of the spring.

The exemplary embodiment discussed above includes a pair of first ribs 166 that are disposed on opposite sides of the circumference of the periphery of the inner hub 162, such that they are spaced approximately 180° from each other. This disposition of the first ribs 166 is advantageous in that it provides substantially uniform retention of the spring 176 and provides for substantially uniform operation of the drive splines, which is discussed in more detail below. However, any number of one or more first ribs 166 can be used. Further, if multiple first ribs 166 are used, then they can be spaced any distance from each other around the circumference of the periphery of the inner hub 162. Still further, the first ribs 166 do not have to include the drive splines 168, the spring retention sections 170 and the spring retention projections 172 discussed above. Instead, the first ribs 166 can be any shape and include any structures to retain the spring 176 and perform the operation of the drive splines, which is discussed in more detail below.

As shown in FIGS. 23-25, the exterior of the inner hub 162 also defines a pair of second ribs 178. The pair of second ribs 178 extend longitudinally and proximally from the annular hub 165 to approximately the longitudinal midpoint of the drive splines 168. A proximal end of the second ribs 178 is tapered.

In operation, the drive splines 168 are received within corresponding channels defined in an interior surface of the gear shaft 74, which is rotated by the motor assembly 38, shown in FIGS. 4-6. Receiving the drive splines 168 within the channels of the gear shaft 74 enables the inner hub 162, and thus the inner tube 130 which is served thereto, to be rotated by the motor assembly 38.

The drive splines 168 are advantageous over some other structures, such as a T-bar arrangement defined at the proximal end of the inner hub 162, in that they provide the inner hub 162 with a relatively large engageable surface area relative to the driving mechanism, i.e., the motor assembly 38 and the gear shaft 74. The drive splines 168 are also advantageous in that they provide for an axial tolerance which may facilitate insertion of the inner hub 162 within the barrel 44 and/or provide other benefits.

However, as discussed above, the drive splines 168 do not have to be used, and instead any other structure can be provided that enables rotation of the inner hub 162. For example, the substantially continuous drive splines 168 shown in the exemplary embodiment can each be replaced with one or more discretely defined blocks, for example. Further, the drive splines can be square, triangular lobes, hex drive, etc.

The cutting blade assembly 8 is intended to be mounted into and secured in the handle 2 in accordance with any acceptable method. For example, the cutting blade assembly 8 can be mounted by pulling the collet assembly 36 rearwardly toward the rear of the handle 2, rotating the hub until the key aligns on the chucking mechanism, inserting the inner hub 162 into the handle 2 until it stops completely, releasing the collet assembly 36 and firmly pushing the cutting blade assembly 8 into the handle 2 until the collet assembly 36 springs back into its original position.

In other words, the inner hub 162 begins to engage the spline geometry of the inner diameter of the drive shaft. As insertion continues, the pair of ribs 140 must be aligned by the operator with any two of the slots present in the fixed lock sleeve 104. The retention sleeve must be retracted as described in the application for any of this to be possible. Otherwise, the retention balls will interfere with the outer hub as it is inserted. After inserting the blade fully, releasing the release ring will allow the retention balls to seat into the dimples on the outer hub. These relative locations are defined by the ribs 140. The retention sleeve is spring loaded and will return to its locked position upon release. The operator should gently pull on the outer tube of the blade assembly to make sure it is properly retained.

The cutting blade assembly 8 can similarly be disengaged from the handle 2. This can be accomplished by pulling the collet assembly 36 rearwardly toward the rear of the handle 2, and then pulling the cutting blade assembly 8 out of the handle 2.

In other words, to remove the blade, the operator must only retract the retention sleeve and pull on the blade. The spring 176 will push the blade assembly out a small amount increasing the amount of outer hub available for handling during removal.

The cutting blade assembly 8 can be disposable. Thus, after a surgical procedure or operation, the cutting blade assembly 8 can be disengaged from the handle 2 as discussed above and disposed of.

After removing the cutting blade assembly 8, the handle 2 and other associated or connected elements that are intended on being reused need to be cleaned and sterilized in an acceptable manner. An exemplary method of cleaning and sterilization is discussed below.

All cleaning should be performed in a manner designed to minimize exposure to blood borne pathogens. Reusable medical devices should be kept moist immediately after use until cleaning. Devices capable of disassembly must be disassembled prior to cleaning. Thorough cleaning and rinsing should be carried out as soon as possible. Manual cleaning should be done while the instrument is immersed (if applicable). The purpose of cleaning and rinsing is to remove all adherent visible soil and to reduce particulate matter, microorganisms and pyrogens. Furthermore, thorough rinsing is necessary to remove any residual cleaning agents from the medical devices that could protect microorganisms from destruction and reduce the lethality of the sterilization process. Medical devices that will be stored between cleaning and decontamination should be dried with low linting, non-abrasive soft cloth to prevent microbial contamination that could result from wet instruments.

Enzymatic detergents with a pH range between 6.0 and 8.0 should be used. These detergents have nonionic surfactants. Detergents should be used at the concentration level recommend by the manufacturer. Undiluted detergents and ones with pHs greater than 8.0 can strip the coloration from metal instruments.

The quality of water should be carefully considered for use in preparing enzymatic detergents and for rinsing in the cleaning procedure. Water hardness is a concern because deposits left on medical devices may result in ineffective cleaning decontamination. Demonized water can help prevent discoloration and staining associated with mineral residues found in tap water.

The handle 2 and/or associated re-usable elements can be cleaned using the exemplary cleaning method as follows:
a) Wipe down the external surface of the handpiece with warm soapy water,
b) Gently scrub the interior of the handpiece using a non-metallic soft bristle brush moistened with the soapy water,
c) Holding the handpiece with the chuck end upwards, flush the interior of the handpiece with running water, to rinse away cleaning residue and loosened debris,
d) Visually inspect and repeat if necessary.

The handle can be sterilized by steam sterilization.

VI. Trigger Switch Assembly

Figure 29:
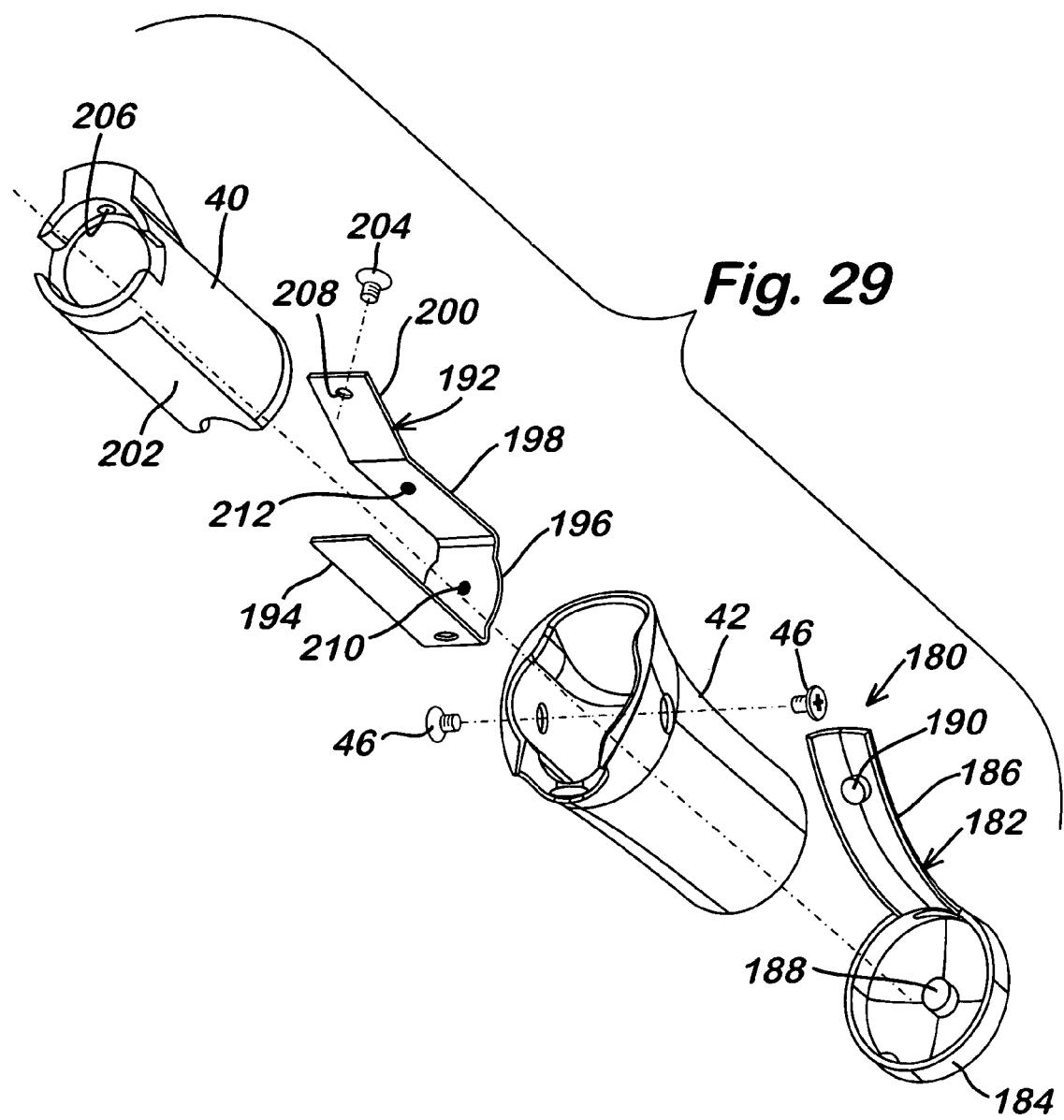
FIG. 29 is an exploded perspective view of the trigger switch assembly 180 and related sub-elements of the handle 2.

Various views of an exemplary embodiment of trigger switch assembly are shown in FIGS. 29-32, wherein FIG. 29 is an exploded perspective view of the trigger switch assembly 180 and related sub-elements of the handle 2, FIG. 30 is a schematic of the sensor strip 192 of the trigger switch assembly 180, FIG. 31 is a side perspective schematic view of the trigger switch assembly 180 mounted on the handle 2, and FIG. 32 is a front schematic view of the trigger switch assembly 180 mounted on the handle 2. An exemplary embodiment of the trigger switch assembly 180 is described below in conjunction with FIGS. 29-32.

The trigger switch assembly 180 can be used in lieu of, or in addition to, the footswitch 4 shown in FIG. 1. As shown in FIGS. 31 and 32, the trigger switch assembly 180 includes an exterior trigger 182 that is disposed at an exterior of the lower portion 34 (specifically the handle shell 42 shown in FIG. 29) of the handle 2. The exterior trigger 182 includes a lower annular end cap 184 that is formed to surround the base of the lower portion 34 (specifically the handle shell 42 shown in FIG. 29) of the handle 2. In fact, the end cap 184 can be sized such that the base of the lower portion 34 can be press fitted into the end cap 184 to secure the exterior trigger 182 to the handle 2.

The exterior trigger 182 also includes an elongated trigger 186. While the lower portion 34 is press fitted to the end cap 184, the elongated trigger 186 extends generally longitudinally along the exterior of the lower portion 34 (specifically the handle shell 42 shown in FIG. 29). The bottom of the elongated trigger 186, which is adjacent to the end cap 184, is either in contact with, or disposed close to, the lower portion 34 of the handle 2. However, the elongated trigger 186 is shaped so that it defines an increasing gap with the lower portion 34 of the handle 2 as it extends upwardly toward the upper portion 32 of the handle 2.

The bottom of the elongated trigger 186, which is adjacent to the end cap 184, forms a fulcrum with regard to the remaining upwardly extending section of the elongated trigger 186. Thus, a surgeon, while grasping the handle 2 as if it was a pistol, can pull an upper section of the elongated trigger 186 toward the lower portion 34 of the handle 2 with one or more of the surgeon's fingers. In this operation, the upper section of the elongated trigger 186 pivots about its bottom.

As shown in FIG. 29, lower magnet 188 is disposed at or on an interior surface of the end cap 184, such that the lower magnet 188 is disposed between the interior surface of the end cap 184 and an exterior surface of the bottom of the handle shell 42 of the lower portion 34 of the handle 2. An upper magnet 190 is disposed at or on an interior surface of the elongated trigger 186, such that the upper magnet 190 is disposed between the interior surface of the elongated trigger 186 and an exterior surface of the handle shell 42 of the lower portion 34 of the handle 2.

While the exterior trigger 182 is attached to the handle shell 42 of the lower portion 34 of the handle 2, the lower magnet 188 remains substantially static relative thereto. However, the distance separating the upper magnet 190 and the handle shell 42 as the surgeon presses the elongated trigger 186 toward the handle shell 42 decreases.

The trigger switch assembly 180 also includes a flexible sensor strip 192 shown in FIGS. 29 and 30. The flexible sensor strip 192 includes a rear portion 194, a bottom portion 196, a lower front portion 198, and an upper front portion 200.

The flexible sensor strip 192 is fixed to the exterior of the handle chassis 40, which is itself disposed inside of the handle shell 42 of the lower portion 34 of the handle 2. A strip of insulation tape 202 is attached to the handle chassis 40 so as to extend longitudinally along a rear surface thereof. The rear portion 194 of the flexible sensor strip 192 contacts and may be connected to the insulation tape 202 as to aid in securing the flexible sensor strip 192 to the handle chassis 40. The bottom of the handle chassis 40 may apply downward pressure to the bottom portion 196 of the flexible sensor strip 192 to also aid in securing the flexible sensor strip 192 to the handle chassis 40. A fastener 204 can also be used to further secure the flexible sensor strip 192 to the handle chassis 40 by extending through an aperture 206 defined in the handle chassis 40 and a corresponding aperture 208 defined in the upper front portion 200 of the flexible sensor strip 192.

The invention is intended to cover any one or more of the above securing methods discussed above. However, the invention is not limited thereto, and any other method of securing the flexible sensor strip 192 to the handle chassis 40 can be used. In fact, the flexible sensor strip 192 does not even have to be secured to the handle chassis 40. Instead, the flexible sensor strip 192 can be statically or substantially statically disposed within the handle shell 42 in accordance with any method or structure.

The flexible sensor strip 192 also includes a lower sensor 210 and an upper sensor 212, which can be Hall sensors that sense a magnetic field. The lower sensor 210 is disposed at or on the bottom portion 196 so as to generally oppose the lower magnet 188. The upper sensor 212 is disposed at or on the lower front portion 198 so as to generally oppose the upper magnet 190. The operation of the lower and upper sensors 210 and 212 is discussed below.

While exterior trigger 182 is secured to the handle shell 42, the lower magnet 188 remains in close proximity to the lower sensor 210. In this state, the lower sensor 210 senses the close proximity of the magnetic field of the lower magnet 188. However, if the exterior trigger 182 is removed and/or spaced from the handle shell, the lower sensor 210 fails to sense the magnetic field of the lower magnet 188. Under this circumstance, the lower sensor 210 can provide an output signal indicating that the exterior trigger 182 is not properly secured to the handle shell 42.

However, the invention is intended to cover any method of determining whether the exterior trigger 182 is properly secured to the handle shell 42. For example, while the exterior trigger 182 is properly secured to the handle shell 42, the lower sensor 210 can continuously provide an appropriate output signal, such that cessation of the output signal can be construed as an indication that the exterior trigger 182 is no longer properly secured to the handle shell 42.

In operation, while the exterior trigger 182 is secured to the handle shell 42, and the surgeon is not actuating the elongated trigger 186, the upper magnet 190 is spaced from the upper sensor 212. However, as the surgeon presses the elongated trigger 186 toward the handle shell 42, the upper magnet 190 moves into close proximity with the upper sensor 212 such that the upper sensor 212 senses its magnetic field. Under this circumstance, the upper sensor 212 can provide an output signal for the purpose of energizing the motor assembly 38 to rotate the inner hub 162 and the inner tube 130. Upon the surgeon releasing the elongated trigger 186, the upper magnet 190 moves away from the upper sensor 212 such that the upper sensor 212 no longer senses the magnetic field of the upper magnet 190. Under this circumstance, the upper sensor 212 ceases providing the output signal such that the motor assembly 38 is de-energized.

The exemplary embodiment of the trigger switch assembly 180 shown in FIGS. 29-32 is especially advantageous over other actuating mechanisms, such as a footswitch, since it is easy for a surgeon to operate. For example, the operation of grasping the handle 2 as a pistol, and pressing the elongated trigger 186 toward the handle shell 42 as if it was the trigger of the pistol, is easier than searching for and depressing a pedal on a footswitch disposed under an operating table.

Further, any or all of the sub-elements of the trigger switch assembly 180 can be manufactured relatively inexpensively. Thus, any or all of the sub-elements of the trigger switch assembly 180 can be considered disposable after one or more operations, which makes sterilization of the apparatus easier and more effective. The disposability of any or all of the sub-elements of the trigger switch assembly 180 is enhanced by the fact that the trigger switch assembly 180 is easy to install at the lower portion 34 of the handle 2. Thus, installing a new trigger switch assembly 180, or a portion thereof, prior to a surgical procedure can be accomplished quickly, easily and/or inexpensively.

However, the invention is intended to cover any method of determining whether the surgeon has pressed the elongated trigger 186 toward the handle shell 42 for the purpose of energizing/de-energizing the motor assembly. Thus, any or all of the elements discussed above can be replaced with other elements to provide this operation. For example, the gap separating the upper section of the elongated trigger 186 can be maintained via a spring or similar compressible mechanism, instead of being maintained by virtue of the shape of the elongated trigger 186. Further, for example, the flexible sensor strip 192 does not have to be flexible, and instead can be rigid and preformed into an appropriate shape, such as that shown in FIG. 29.

Further, the elongated trigger 186, the upper magnet 190 and the upper sensor 212 can be used to also control the speed of rotation of the motor assembly 38. For example, the further the surgeon presses the elongated trigger 186, causing the upper magnet 190 to become incrementally or gradually closer to the upper sensor 212, can cause the upper sensor 212 to provide output signals to increase the speed of rotation of the motor assembly 38. Similarly, the surgeon gradually releasing pressure on the elongated trigger 186 may cause the upper sensor 212 to provide output signals to decrease the speed of rotation of the motor assembly 38.

VII. Footswitch

FIG. 33 is a perspective view showing the exterior of an exemplary embodiment of the footswitch 4 in accordance with the invention. The exemplary embodiment of the footswitch 4 is described below in conjunction with FIG. 33.

The footswitch 4 includes a base 214 which is supported on the floor of the surgical room by feet 216, sides 218 disposed on or above a rear portion of the base 214, and a top 220 disposed on or above the sides 218.

The foot pedal 12 is movably supported in an upright orientation via a bar assembly 222 that extends through apertures defined in the sides 218. A spring or any other mechanism can be used with, or in lieu of, the bar assembly 222 to support the foot pedal 12 in this orientation. The foot pedal 12 is operationally connected to a signal generating device (not shown) disposed in the space defined by the sides 218 and the top 220, such that depressing the foot pedal 12 so that it rotates downwardly about the bar assembly 222 causes the signal generating device to generate an input signal to be input to the controller 6 via the footswitch signal line 10.

In operation, the surgeon, after placing the heel or his or her foot on or adjacent to the front of the base 214, depresses the foot pedal 12 with the front and/or toes of the surgeon's foot so that the foot pedal 12 rotates downwardly toward the base 214. After a predetermined amount of rotation, the signal generating device (not shown) is actuated to provide an appropriate input signal to the controller 6 via the footswitch signal line 10. Upon receipt of the appropriate input signal, the controller 6 outputs an output signal to the motor assembly 38 of the handle 2 via the handle signal line 14 to energize the motor assembly 38 and thereby rotate the inner hub 162 and inner tube 130. Releasing the foot pedal 12 enables it to rotate back to its upright orientation, thereby causing the signal generating device to provide an appropriate input signal to the controller 6, which in turn de-energizes the motor assembly 38.

The footswitch 4 can also include a light (not shown). The light can be disposed at an appropriate location and be of a sufficient brightness to illuminate all or a part of the footswitch 4. Illuminating the footswitch 4 in this manner is advantageous over non-lighted footswitches, or footswitches that only include LED's for indicating on/off status, in that it enables the surgeon to more easily find the lighted footswitch 4, which may be disposed among other footswitches and similar devices during surgery or in a surgical room. This advantage is enhanced if the footswitch 4 is provided with a light of a distinctive color, such as blue, for example.

The base 214 of the footswitch 4 can also define an opening 224 which can be used for a variety of purposes. For example, the opening 224 can be used by the surgeon to reorient the footswitch 4, or maintain the surgeon's foot at an appropriate position during operation. The opening 224 can also be used to hang the footswitch up in a vertical orientation when not in operation.

The footswitch 4 can also include a button 225 to perform an operation. For example, the button 225 can actuate the creation of an input signal to be input to the controller 6 for the purpose of changing the mode of operation of the cutting blade assembly 8. For example, the controller 6 can actuate the motor assembly 38 between a constant mode where the inner hub 162 and the inner tube 130 are rotated at a constant or substantially constant speed, and a variable mode where the inner hub 162 and the inner tube 130 are rotated at a variable speed.

The invention is not limited to the structure of the footswitch 4 discussed above. The invention is intended to cover any method of providing an appropriate input signal to the controller 6 enabling the controller 6 to perform an operation, such as to energize/de-energize the motor assembly 38, for example.

Further, the footswitch 4 can be used to send other types of input signals to the controller 6 via the footswitch signal line 10. For example, the signal generating device may provide the controller 6 with a variable input signal based upon the amount of depression of the foot pedal 12 to vary the speed of rotation of the inner hub 160 and the inner tube 130.

VIII. Integrated Strippable Twin Tubing

Figure 34:
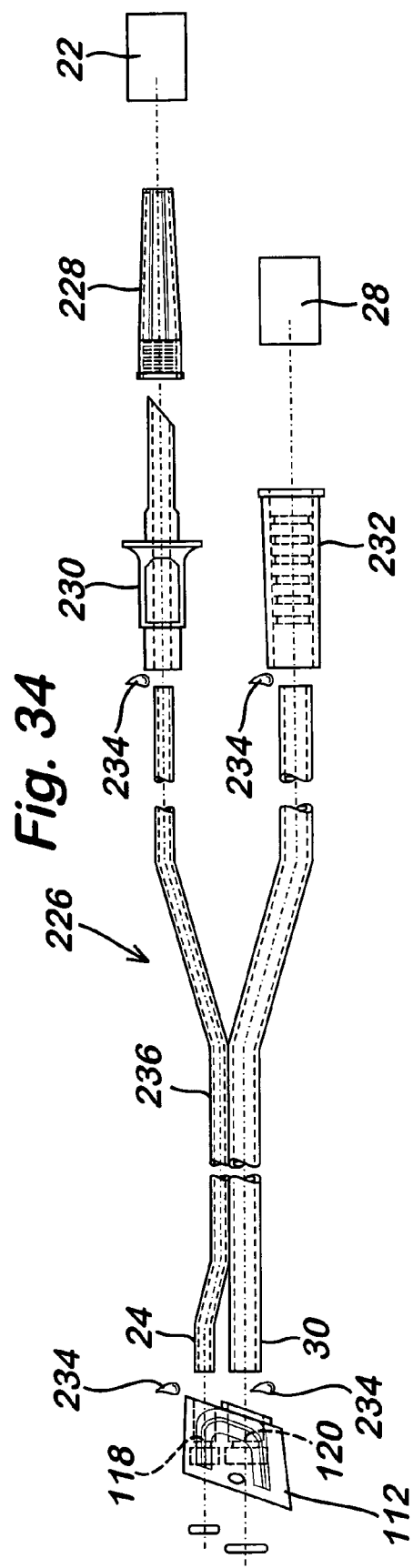
FIG. 34 is a perspective view of the twin tubing 226 as well as devices connected thereto.
Figure 35:
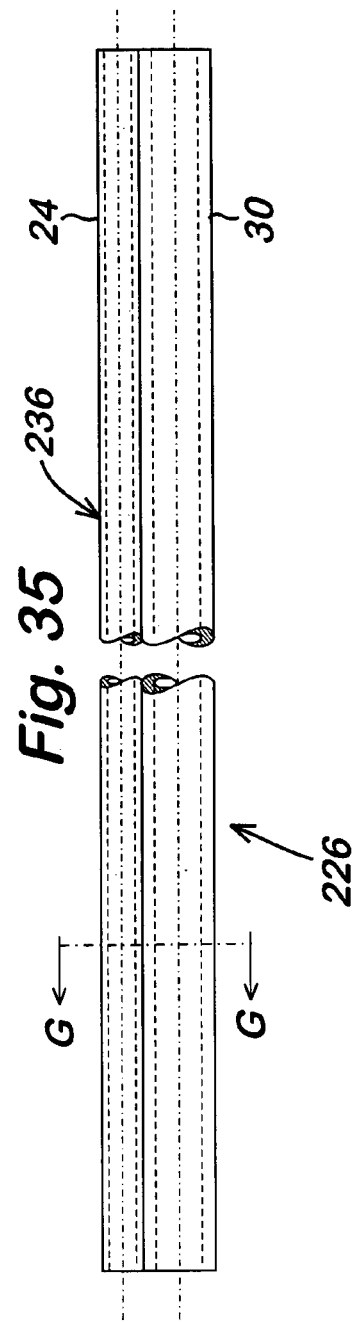
FIG. 35 is a perspective view showing a section 236 of the twin tubing 226 in a connected state.
Figure 36:
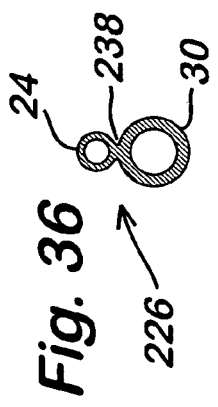
FIG. 36 is a sectional view of the twin tubing 226 taken along plane G-G of FIG. 35.

The irrigation fluid supply tube 24 and the suction supply tube 30 can be provided as integrated strippable twin tubing 226. Various views of an exemplary embodiment of the twin tubing are shown in FIGS. 34-36, wherein FIG. 34 is a perspective view of the twin tubing 226 as well as devices connected thereto, FIG. 35 is a perspective view showing a section 236 of the twin tubing 226 in a connected state, and FIG. 36 is a sectional view of the twin tubing 226 taken along plane G-G of FIG. 35. An exemplary embodiment of the twin tubing 226 is discussed below in conjunction with FIGS. 34-36.

The twin tubing 226 can be disposable. Thus, the twin tubing 226 can be disposed of subsequent to each surgical procedure or operation.

As shown in FIG. 34, the irrigation fluid supply tube 24 supplies irrigation fluid from the irrigation fluid source 22, via a vented spike cap 228 and a non-vented irrigation spike 230, to the irrigation fluid entry channel 118 of the tube connector 112 that is provided at the rear end of the upper portion 32 of the handle 2. The suction supply tube 30 supplies suction from the suction source 28, via a suction connector 232, to the suction entry channel 120 of the tube connector 112. Adhesive 234 can be used to connect the irrigation fluid supply tube 24 to the tube connector 112 and the non-vented irrigation spike 230, as well as the suction supply tube 30 to the tube connector 112 and the suction connector 232.

The twin tubing 226 can have an integrated tubing portion 236, wherein the irrigation fluid supply tube 24 is connected to the suction supply tube 30 via a connection section 238. FIGS. 35 and 36 specifically show the integrated tubing portion 236 as well as the connection section 238. The integrated tubing portion 236 keeps the irrigation fluid supply tube 24 and the suction supply tube 30 together, which saves space and/or enhances organization in and/or around the surgical area.

The connection section 238 can be split, separated and/or stripped so as to separate the irrigation fluid supply tube 24 and the suction supply tube 30. As shown in FIG. 34, the tubes 24 and 30 can be separated at or near their ends to facilitate their respective direct or indirect connections to the tube connector 112, irrigation fluid source 22 and suction source 28. However, the tubes 24 and 30 can be separated at any other location or for any other purpose.

Although the integrated strippable twin tubing 226 provides advantages as discussed above, the invention is intended to cover any other medium to supply irrigation fluid and suction to the handle 2. For example, the tubes 24 and 30 can be either completely separated or completely connected across their entire lengths. Also, one or more of the vented spike cap 228, the non-vented irrigation spike 230 and the suction connector 232 can either be obviated or replaced with any appropriate structure to facilitate or accomplish any purpose.

Further, FIGS. 34-36 show the irrigation fluid supply tube 24 as being smaller than the suction supply tube 30. However, the invention is intended to cover each of the tubes 24 and 30 as being any respective size. The irrigation fluid supply tube 24 is also shown as being disposed above the suction supply tube 30. However, the invention is intended to cover any respective orientation between the tubes 24 and 30.

In the exemplary embodiment, the irrigation fluid supply tube 24 is manufactured from a deformable material, such as a rubber-based material, for example. This material is advantageous since it facilitates connection to the various devices and enables the use of a simple irrigation fluid supply mechanism 26. However, the irrigation fluid supply tube 24 can be manufactured from any other material, such as a semi-deformable or non-deformable material.

IX. Irrigation Fluid Supply Mechanism

Figure 37:
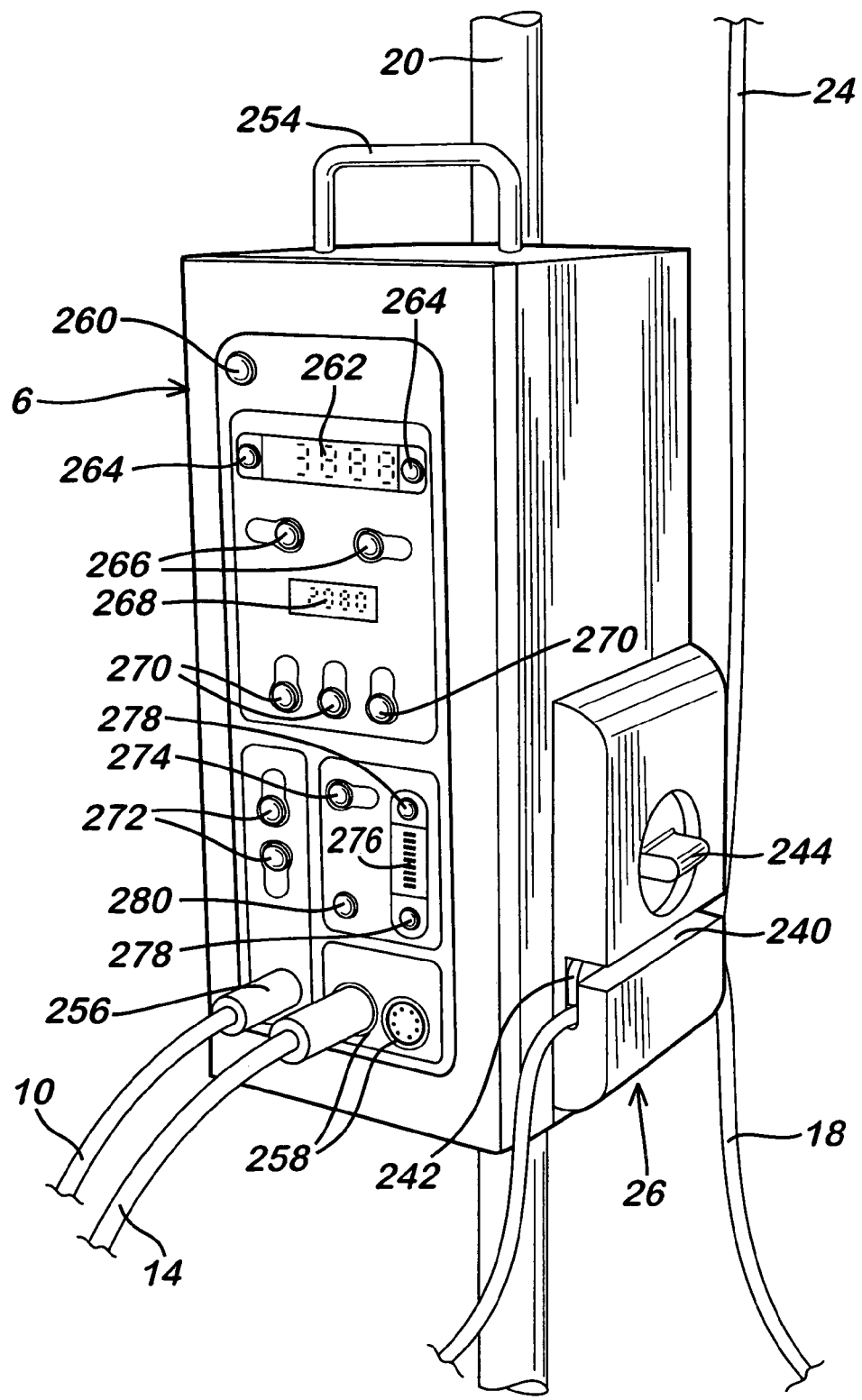
FIG. 37 is a perspective view showing the front of the controller 6 and the irrigation fluid supply mechanism 26.
Figure 38:
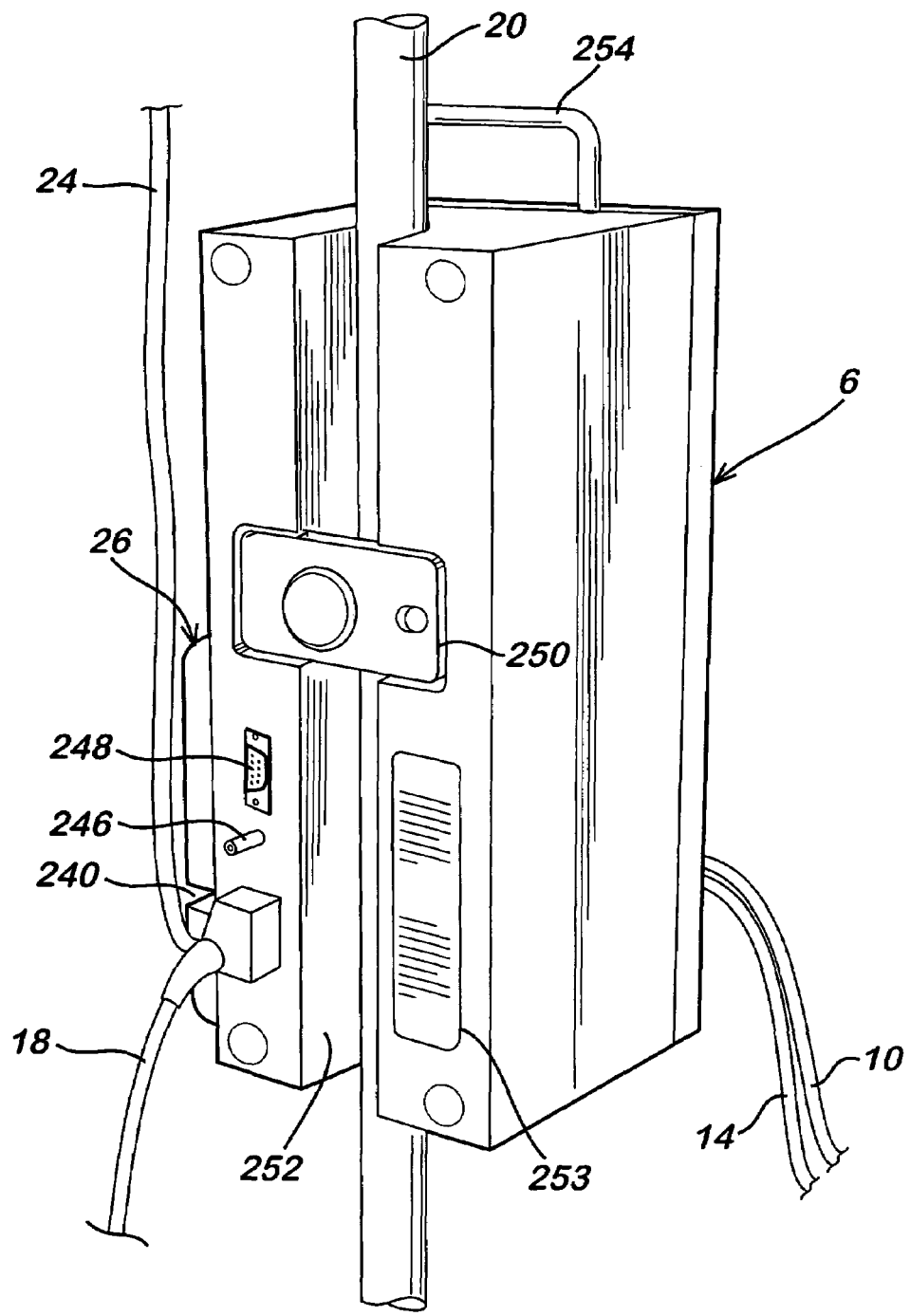
FIG. 38 is a perspective view showing the rear of the controller 6 and the irrigation fluid supply mechanism 26.

Various views of an exemplary embodiment of the irrigation fluid supply mechanism 26 are shown in FIGS. 37 and 38, wherein FIG. 37 is a perspective view showing the front of the irrigation fluid supply mechanism 26, and FIG. 38 is a perspective view showing the rear of the irrigation fluid supply mechanism 26. An exemplary embodiment of the irrigation fluid supply mechanism 26 is discussed below in conjunction with FIGS. 37 and 38.

The exemplary embodiment of the irrigation fluid supply mechanism 26 supplies irrigation fluid from the irrigation fluid source 22, via the irrigation fluid supply tube 24, to the irrigation fluid entry channel 118 of the tube connector 112 that is provided at the rear end of the upper portion 32 of the handle 2 (refer to FIGS. 1 and 12). As shown in FIGS. 37 and 38, the exemplary embodiment of the irrigation fluid supply mechanism 26 is disposed at or on a side of the controller 6.

However, the irrigation fluid supply mechanism 26 does not have to be disposed at this location. Instead, the irrigation fluid supply mechanism can be disposed at any location, such as at or on the irrigation fluid source 22.

As shown in FIGS. 37 and 38, the irrigation fluid supply mechanism 26 defines a tube channel 240 through which the irrigation fluid supply tube 24 extends. The tube channel 240 can be an inverted L-shape that includes a horizontal portion and a vertical portion. The irrigation fluid supply tube 24 can be inserted into the tube channel 240 via the horizontal portion and ultimately disposed at the bottom of the vertical portion.

The irrigation fluid supply mechanism 26 also includes a cam 242 that is extendible into the vertical portion of the tube channel 240. The cam 242 can increase the pressure of the irrigation fluid supplied to the handle 2 by extending into the vertical portion of the tube channel 240 and contacting the irrigation fluid supply tube 24 disposed therein so as to compress and thereby reduce the opening defined by the inner diameter of the tube 24. Thus, the cam 242 presses one side of the irrigation fluid supply tube 24 while the opposite side of the tube 24 is held against the bottom surface of the vertical portion of the tube channel 240. Reducing the inner diameter of the irrigation fluid supply tube 24 correspondingly increases the pressure of the irrigation fluid supplied to the handle 2. Similarly, the pressure of the irrigation fluid supplied to the handle 2 can be reduced by moving the cam 242 out of contact with the irrigation fluid supply tube 24 so as to increase its inner diameter.

The amount of contact pressure provided by the cam 242 to the irrigation fluid supply tube 24 can be varied to supply irrigation fluid to the handle 2 at a specific pressure. An embodiment enables the contact pressure, and thus the irrigation fluid supply pressure, to be manually regulated by a knob 244. The knob 244 communicates with the cam 242, such that rotating the knob 244 in one direction, such as clockwise, for example, moves the cam 242 downwardly within the vertical portion of the tube channel 240 and into contact with the irrigation fluid supply tube 24, while rotating the knob 244 in the opposite direction, such as counterclockwise, for example, moves the cam 242 upwardly and away from the tube 24. Thus, by manually rotating the knob 244, the surgeon or member of the surgical team, may provide the desired irrigation fluid supply pressure. However, in another exemplary embodiment, the knob 244 is only used to move the cam 242 out of the way to enable insertion of the irrigation fluid supply 24, and the irrigation fluid supply mechanism 26 is controlled by the controller 6 to provide a desired fluid pressure.

Although the exemplary embodiment of the irrigation fluid supply mechanism 26 is described above as utilizing a cam mechanism, the invention is intended to cover any method of supplying irrigation fluid to the handle 2. For example, the irrigation fluid supply mechanism 26 can be a rotary type peristaltic pump. In fact, the invention is even intended to cover an apparatus that does not utilize irrigation fluid.

X. Controller

Various views of an exemplary embodiment of the controller 6 are shown in FIGS. 37 and 38, wherein FIG. 37 is a perspective view showing the front of the controller 6, and FIG. 38 is a perspective view showing the rear of the controller 6. An exemplary embodiment of the controller 6 is discussed below in conjunction with FIGS. 37 and 38.

In accordance with an exemplary embodiment or the apparatus, the controller 6 can be used to receive input signals and/or provide output signals relevant to the operation of the apparatus. The controller 6 can be an electronic device to provide this function. Thus, as shown in FIG. 38, the power source supply line 18 can be plugged into the rear of the controller 6. A source of AC or DC power can be provided to the controller 6 from the power source 16 via the power source supply line 18 to supply power for operation of the controller 6. For example, the controller can operate from a source of 100-240 VIC, 50-60 Hz. However, the remote power source 16 can be replaced with a power source that is integral with the controller 6, such as a battery, for example.

The body of the controller 6 can be made from any material. For example, the body of the controller 6 can be molded from flame retardant plastic (synthetic resin).

The controller 6 can also include a grounding post 246, as well as a serial port 248 for connection to any electronic device. A label 253 providing relevant data can also be provided at the rear of the controller 6.

As shown in FIG. 38, the controller is vertically mounted in the surgical room at or on a vertical rail 20, such as an IV pole, that extends through a mounting channel 252 defined in the rear of the controller 6. An attachment clamp 250 can be provided to secure the controller 6 in place on the vertical rail 20. The controller 6 can be movably mounted at or on the vertical rail 20, and may include a handle 254 provided at its upper surface to facilitate an operator manually moving the controller 6 along the vertical rail 20.

Movably mounting the controller 6 on the vertical rail 20 is advantageous in that it enhances viewability of the controller 6 and may satisfy space constraints. However, the controller 6 does not have to be mounted on the vertical rail 6, and instead can be mounted to anything or anywhere. The controller 6 does not even have to be mounted on anything, and can be disposed on the surgical room floor, for example. In fact, the controller 6 can even be disposed remote from the surgical site.

As shown in FIG. 37, the front face of the controller 6 can be used to provide various input/output connections, buttons, and displays, for example, which are discussed below. For example, the footswitch signal line 10 can be connected to the controller 6 via a footswitch input connector 256, which enables various sub-elements of the footswitch 4, such as the signal generating device, for example, to send and/or receive signals to/from the controller 6. If the trigger switch assembly 180 is used in lieu of, or in addition to, the footswitch 4, it can similarly be connected to the controller 6. Handle input connectors 258 can also be provided for connection of the handle signal line 14 to the controller 6, which enable the controller 6 to send and/or receive signals to/from sub-elements of the handle 2, such as to energize/de-energize the motor assembly 38, and/or to receive identification information to enable the controller 6 to determine the type of handle 2 current being used, which can be provided by an EEPROM. Multiple handle input connectors 258 can be provided to enable the connection of multiple handles 2 to the controller 6.

The front face of the controller 6 can also include a power on/off button 260 to turn the controller 6 on/off. If the type of handle 2 is determined, a display 262 can display the maximum RPM provided by the motor assembly 38 of the identified handle 2. Handle speed adjustment buttons 264 can be provided to increase/reduce the speed of rotation of the inner hub 162 and the inner tube 130.

Active handle selection buttons 266 can also be provided if multiple handles 2 are connected to the controller 6 via the handle input connectors 258. In this circumstance, pressing either of the active handle selection buttons 266 can select one of the connected handles 2 for operation.

Another display 268 can also be provided on the front face of the controller 6 to display the actual handle 2 RPM. Specifically, this display 268 indicates the actual or current RPM being provided by the motor assembly 38 to rotate the inner hub 162 and the inner tube 130 of the cutting blade assembly 8.

Handle operating mode buttons 270 can be provided to change the operating mode of the handle 2. For example, these buttons 270 can be used to change the rotation of the inner hub 162 and the inner tube 130 of the cutting blade assembly 8 between a forward direction, a reverse direction, and/or an oscillating type of rotation.

Footswitch operating mode buttons 272 can also be provided to change the mode of operation of the footswitch 4. For example, these buttons 272 can be used to actuate the footswitch 4 between a constant mode, wherein any depression of the foot pedal 12 results in a constant speed of rotation of the inner hub 162 and the inner tube 130 of the cutting blade assembly 8, and a variable mode, wherein the amount of depression of the foot pedal 12 varies the speed of rotation of the inner hub 162 and the inner tube 130.

An irrigating pump on/off button 274 can be provided to enable the irrigation fluid supply mechanism 26 to provide irrigation fluid to entry channel 118 of the tube connector 112 at the handle 2, or prevent the supply thereof. An irrigation pump flow rate display 276 can be provided to indicate the irrigation fluid flow rate currently being provided by the irrigation fluid supply mechanism 26. Irrigation pump flow rate buttons 278 can further be provided in lieu of, or in addition to, the knob 244, to increase/decrease the irrigation fluid flow rate provided by the irrigation fluid supply mechanism 26. If the knob 244 is used in conjunction with the irrigation fluid flow rate buttons 278, the knob 244 may solely be used to move the cam 242 out of the way to enable insertion of the irrigation fluid supply tube 24 into the vertical portion of the tube channel 240, for example. An irrigation pump prime button 280 can also be provided to prime the irrigation fluid supply mechanism 26. Specifically, activating this button 280 allows continuous operation of the irrigation fluid supply mechanism 26 to fill all tubing and/or the handle 2 with irrigation fluid to facilitate easy set-up of the irrigation fluid supply mechanism 26.

Various input/output connections, buttons and displays have been discussed above in the context of the exemplary embodiment of the controller 6 shown in FIGS. 37 and 38. However, the invention is intended to cover any method of performing the functions discussed above. In fact, the invention is intended to cover any method of providing any relevant function in relation to the surgical apparatus.

The controller 6 can be configured so as to be divided into two main components, such as a handle motor controller and a coordinating/main controller. The handle motor controller can contain an embedded module that implements its particular responsibilities and provides an interface to the main controller.

The main controller can be responsible for managing the user interface and related device configuration, detecting the presence and type of handle 2 and other peripheral components, and coordinating the response of the handle 2, and the irrigation fluid supply mechanism 26 in response to user input. Because of the simplicity of the device, the main controller can be directly responsible for the control of the irrigation fluid supply mechanism 26.

The handle controller can be responsible for meeting most of the performance and safety requirements of the handle 2. It can directly control the motor assembly 38 and can interpret high-level commands from the main controller into the appropriate signals to provide forward, reverse and oscillating rotation of the motor assembly 38 at the required speed. The handle controller can also be responsible for detecting faults in the motor assembly 38 and responding to them appropriately.

While this invention has been described in conjunction with the exemplary embodiments outlined above, it is evident that many alternatives, modifications and variations will be apparent to those skilled in the art. Accordingly, the exemplary embodiments of the invention as set forth above are intended to be illustrative and not limiting. Various changes may be made without departing from the spirit and scope of the invention as defined in the following claims.

What is claimed is:

1. A handle assembly usable as a powered surgical apparatus with a source of suction and a source of irrigation fluid, comprising:
    a movable cutting blade assembly that includes a rotatable inner tube defining a cutting surface and an outer tube defining a cutting window, the inner tube extending within the outer tube so as to define a tube gap therebetween;
    a handle having an upper portion and a lower portion, the upper portion defining a distal section that is connectable to the movable cutting blade assembly, the upper portion defining a integral proximal end having a suction coupling and an irrigation fluid coupling, the suction coupling and the irrigation fluid coupling each forming a proximally extending convex projection, the handle defining an irrigation fluid channel that extends from the irrigation fluid coupling to the cutting blade assembly, and a suction channel extending from the suction coupling to the cutting blade assembly, the irrigation fluid channel being in fluid communication with the tube gap; and
    a connector connected to the proximal end of the handle at the irrigation fluid coupling and the suction coupling, the connector defining an irrigation fluid entry channel that is contiguous with the irrigation fluid channel of the handle, and a suction entry channel that is contiguous with the suction channel of the handle.

2. The handle assembly according to claim 1, wherein the lower portion extends downwardly from the upper portion so as to define an angle of less than 90° with the distal section of the upper portion.

3. The handle assembly according to claim 1, further including a motor assembly, at least a portion of the motor assembly being disposed within the lower portion.

4. The handle assembly according to claim 1, wherein the distal section of the upper portion includes a movably rotatable collet assembly, the collet assembly being connectable to the outer tube such that manual rotation of the collet assembly results in rotation of the outer tube and thereby reorientation of the cutting window.

5. The handle assembly according to claim 1, wherein the upper portion is connectable to the movable cutting blade that is structured so as to be usable in sinus surgery.

6. The handle assembly according to claim 1, wherein the suction channel extends along a substantially straight path through the upper portion.

7. The handle assembly according to claim 1, wherein the suction entry channel is adjacent and vertically spaced from the irrigation fluid entry channel.

8. The handle assembly according to claim 1, the upper portion defining at least one detent that is engageable with at least one aperture defined in the connector to secure the connector to the upper portion.

9. The handle assembly according to claim 8, wherein the at least one detent includes two detents that are disposed on circumferentially opposite sides of the upper portion, and the at least one aperture includes two apertures defined in the connector at locations corresponding to the two detents.

10. The handle assembly according to claim 8, the connector defining at least one gripping portion adjacent to the at least one aperture.

11. The handle assembly according to claim 10, wherein the at least one gripping portion is at least one channel defined in an exterior surface of the connector.

12. The handle assembly according to claim 1, wherein the connector is defined by a periphery that corresponds to a periphery of the proximal end of the upper portion such that the upper portion and the connector form a substantially uniform exterior.

13. The handle assembly according to claim 1, wherein the handle assembly is usable with an irrigation fluid supply tube connected to the source of irrigation fluid and a suction supply tube connected to the source of suction, the irrigation fluid entry channel of the connector defining an irrigation fluid entry coupling that is connectable to the irrigation fluid supply tube, and the suction entry channel of the connector defining a suction entry coupling that is connectable to the suction supply tube.

14. The handle assembly according to claim 1, the connector being formed of synthetic resin.

15. A method of manufacturing a handle assembly that is usable as a powered surgical apparatus, comprising:
    forming a handle having an upper portion and a lower portion, the upper portion defining a distal section that is connectable to a movable cutting blade assembly, the movable cutting blade assembly including a rotatable inner tube defining a cutting surface and an outer tube defining a cutting window, the inner tube extending within the outer tube so as to define a tube gap therebetween;
    forming an irrigation fluid coupling and a suction coupling at a proximal end of the upper portion, the irrigation fluid coupling, the suction coupling, and the proximal end of the upper portion being integral with the upper portion, the irrigation fluid coupling and the suction coupling each forming a proximally extending convex projection;
    forming an irrigation fluid channel in the handle from the irrigation fluid coupling to the cutting blade assembly, the irrigation fluid channel being in fluid communication with the tube gap;
    forming a suction channel in the handle from the suction coupling to the cutting blade assembly;
    connecting a connector to the proximal end of the handle at the irrigation fluid coupling and suction coupling;
    forming an irrigation fluid entry channel in the connector that is contiguous with the irrigation fluid channel of the handle; and
    forming a suction entry channel in the connector that is contiguous with the suction channel of the handle.

16. A handle assembly usable as a powered surgical apparatus with a source of suction and a source of irrigation fluid, comprising:
    a movable cutting blade assembly that includes a rotatable inner tube defining a cutting surface and an outer tube defining a cutting window;
    a handle having an upper portion and a lower portion, the upper portion defining a distal section that is connectable to the movable cutting blade assembly, the upper portion defining a proximal end that defines a suction coupling and an irrigation fluid coupling, the handle defining an irrigation fluid channel that extends from the irrigation fluid coupling to the cutting blade assembly, and a suction channel extending from the suction coupling to the cutting blade assembly;
    a movably rotatable collet assembly at the distal section of the upper portion of the handle, the collet assembly being connectable to the outer tube such that manual rotation of the collet assembly results in rotation of the outer tube and thereby reorientation of the cutting window; and
    a connector connected to the proximal end of the handle at the irrigation fluid coupling and the suction coupling, the connector defining an irrigation fluid entry channel that is contiguous with the irrigation fluid channel of the handle, and a suction entry channel that is contiguous with the suction channel of the handle.

17. A handle assembly usable as a powered surgical apparatus with a source of suction and a source of irrigation fluid, comprising:
    a movable cutting blade assembly that includes a rotatable inner tube defining a cutting surface and an outer tube defining a cutting window;
    a handle having an upper portion and a lower portion, the upper portion defining a distal section that is connectable to the movable cutting blade assembly, the distal section of the upper portion including a movably rotatable collet assembly, the collet assembly being connectable to the outer tube such that manual rotation of the collet assembly results in rotation of the outer tube and thereby reorientation of the cutting window, the upper portion defining a proximal end that defines a suction coupling and an irrigation fluid coupling, the handle defining an irrigation fluid channel that extends from the irrigation fluid coupling to the cutting blade assembly, and a suction channel extending from the suction coupling to the cutting blade assembly, the upper portion defining at least one detent; and
    a connector connected to the proximal end of the handle at the irrigation fluid coupling and the suction coupling, the connector defining an irrigation fluid entry channel that is contiguous with the irrigation fluid channel of the handle, and a suction entry channel that is contiguous with the suction channel of the handle, the connector defining at least one aperture that is engageable with the at least one detent to secure the connector to the upper portion of the handle.

18. The handle assembly according to claim 17, wherein the at least one detent includes two detents that are disposed on circumferentially opposite sides of the upper portion, and the at least one aperture includes two apertures defined in the connector at locations corresponding to the two detents.

19. The handle assembly according to claim 17, the connector defining at least one gripping portion adjacent to the at least one aperture.

20. The handle assembly according to claim 19, wherein the at least one gripping portion is at least one channel defined in an exterior surface of the connector.

21. The handle assembly according to claim 1, the irrigation fluid entry channel of the connector defining a concave space that receives the irrigation fluid coupling, and the suction entry channel of the connector defining a concave space that receives the suction coupling.

* * * * *